US012700476B2

(12) United States Patent
Luo et al.

(10) Patent No.: US 12,700,476 B2
(45) Date of Patent: Aug. 4, 2026

(54) METHODS AND SYSTEMS FOR ENHANCING NUCLEIC ACID SEQUENCING QUALITY IN HIGH-THROUGHPUT SEQUENCING PROCESSES WITH MACHINE LEARNING

(71) Applicant: GeneSense Technology Inc., Shanghai (CN)

(72) Inventors: Shaobo Luo, Shanghai (CN); Zhiyuan Xie, Shanghai (CN); Gengxin Chen, Shanghai (CN); Tianzhen Ao, Shanghai (CN); Mei Yan, Shanghai (CN)

(73) Assignee: GENESENSE TECHNOLOGY INC., Shanghai (CN)

( * ) Notice: Subject to any disclaimer, the term of this patent is extended or adjusted under 35 U.S.C. 154(b) by 0 days.

(21) Appl. No.: 18/070,377

(22) Filed: Nov. 28, 2022

(65) Prior Publication Data

US 2024/0013861 A1 Jan. 11, 2024

Related U.S. Application Data

(63) Continuation of application No. PCT/CN2022/104105, filed on Jul. 6, 2022.

(51) Int. Cl.
*G16B 30/00* (2019.01)
*G16B 40/20* (2019.01)

(52) U.S. Cl.
CPC ............. *G16B 30/00* (2019.02); *G16B 40/20* (2019.02)

(58) Field of Classification Search
None
See application file for complete search history.

(56) References Cited

U.S. PATENT DOCUMENTS

| 10,068,053 | B2 | 9/2018 | Kermani et al. |
| 11,288,576 | B2 | 3/2022 | Dutta et al. |
| 2022/0067489 | A1 | 3/2022 | Kashefhaghighi et al. |

FOREIGN PATENT DOCUMENTS

| CN | 110892484 | A | 3/2020 |
| CN | 114664379 | A | 6/2022 |
| WO | 2022/040573 | A2 | 2/2022 |

OTHER PUBLICATIONS

Poplin, Ryan, et al. "A universal SNP and small-indel variant caller using deep neural networks." Nature biotechnology 36.10 (2018): 983-987.*
International Search Report and Written Opinion issued in International Application No. PCT/CN2022/104105 dated Dec. 28, 2022, 10 pages.

* cited by examiner

*Primary Examiner* — G. Steven Vanni
(74) *Attorney, Agent, or Firm* — MASCHOFF BRENNAN; Michael Mauriel; Liang Huang

(57) ABSTRACT

This disclosure provides an improved filtering techniques that can provide higher sequencing accuracy for processing high-throughput sequencing data. The filtering structure uses a hierarchical network structure comprising one or more network blocks for obtaining high quality sequences. Each network block comprises a base network module (or simply a base network) and a sequence filter. The base network generates one or more sequencing quality indicators. The sequencing quality indicators can represent qualities of accuracy of the basecalling of individual bases in a sequence, the quality of one or more sequences individually, or the quality of a group of sequences as a whole. The sequence filter generates the filtered results based on the various filtering strategies based on the one or more sequencing quality indicators.

17 Claims, 17 Drawing Sheets

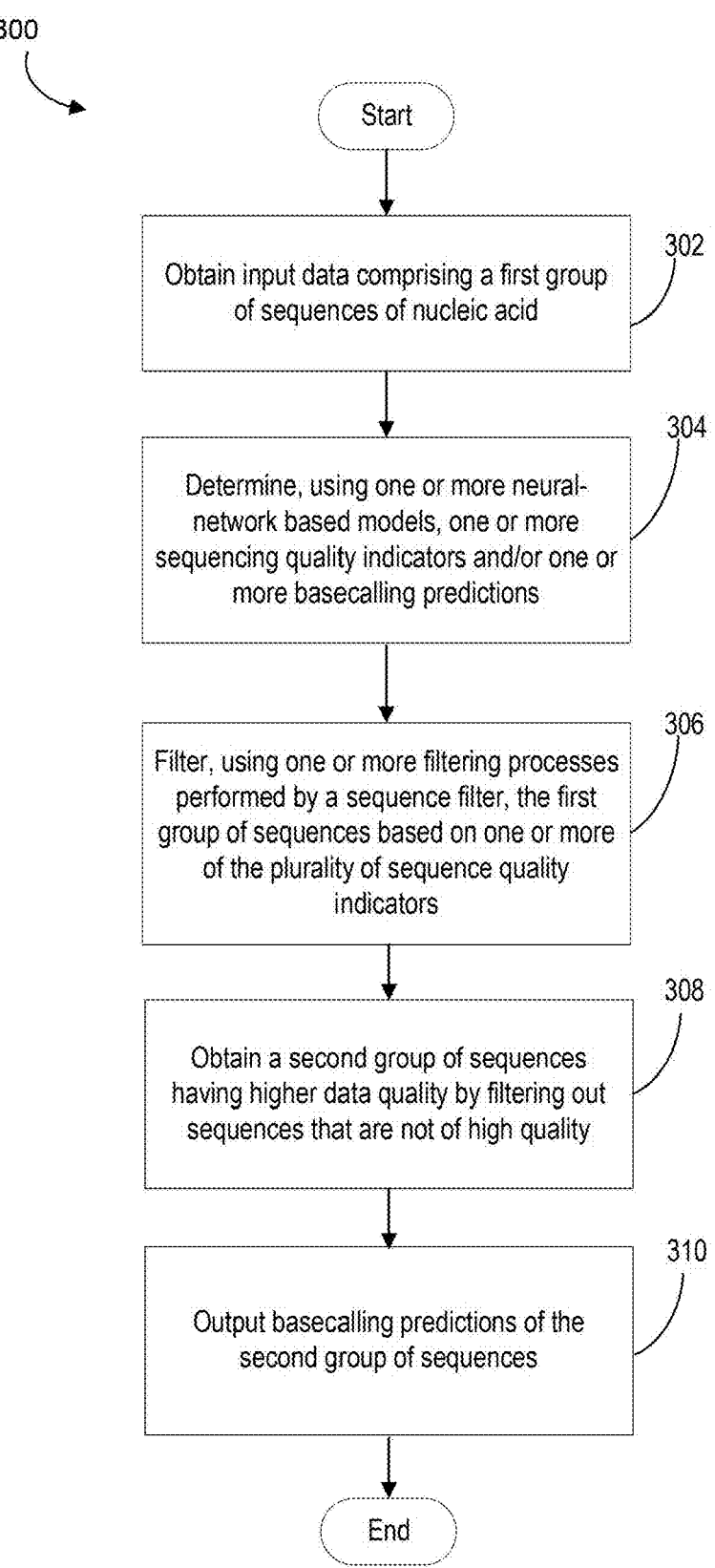

300

Start

Obtain input data comprising a first group of sequences of nucleic acid                    302

Determine, using one or more neural-network based models, one or more sequencing quality indicators and/or one or more basecalling predictions                    304

Filter, using one or more filtering processes performed by a sequence filter, the first group of sequences based on one or more of the plurality of sequence quality indicators                    306

Obtain a second group of sequences having higher data quality by filtering out sequences that are not of high quality                    308

Output basecalling predictions of the second group of sequences                    310

End

FIG. 3

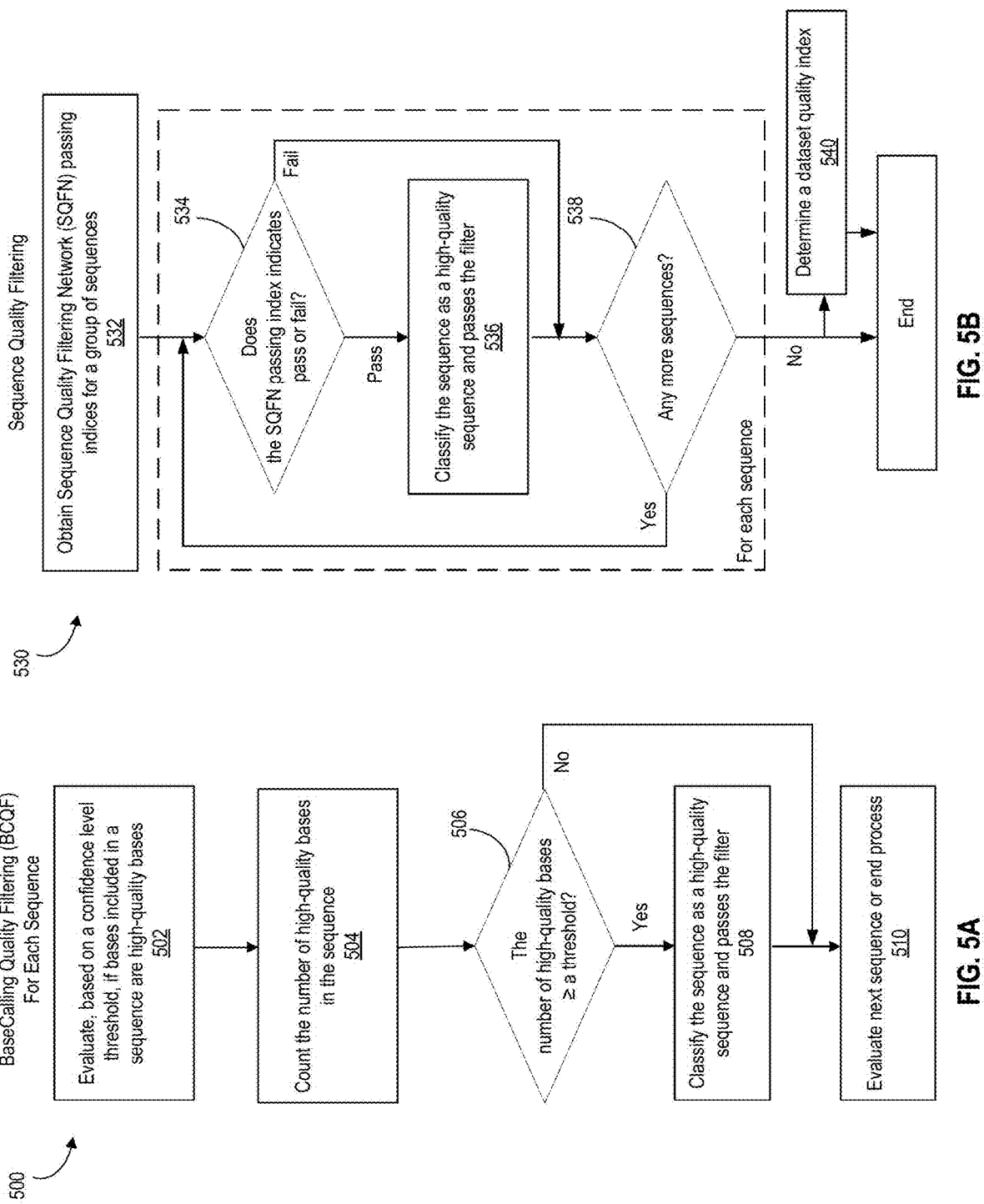

Sequence Quality Filtering

Obtain Sequence Quality Filtering Network (SQFN) passing indices for a group of sequences
532

534

Does the SQFN passing index indicates pass or fail?

Fail

Pass

Classify the sequence as a high-quality sequence and passes the filter
536

538

Any more sequences?

Yes

No

For each sequence

Determine a dataset quality index
540

End

BaseCalling Quality Filtering (BCQF) For Each Sequence

Evaluate, based on a confidence level threshold, if bases included in a sequence are high-quality bases
502

Count the number of high-quality bases in the sequence
504

506

The number of high-quality bases ≥ a threshold?

No

Yes

Classify the sequence as a high-quality sequence and passes the filter
508

Evaluate next sequence or end process
510

Label Filtering on Training
Dataset
600

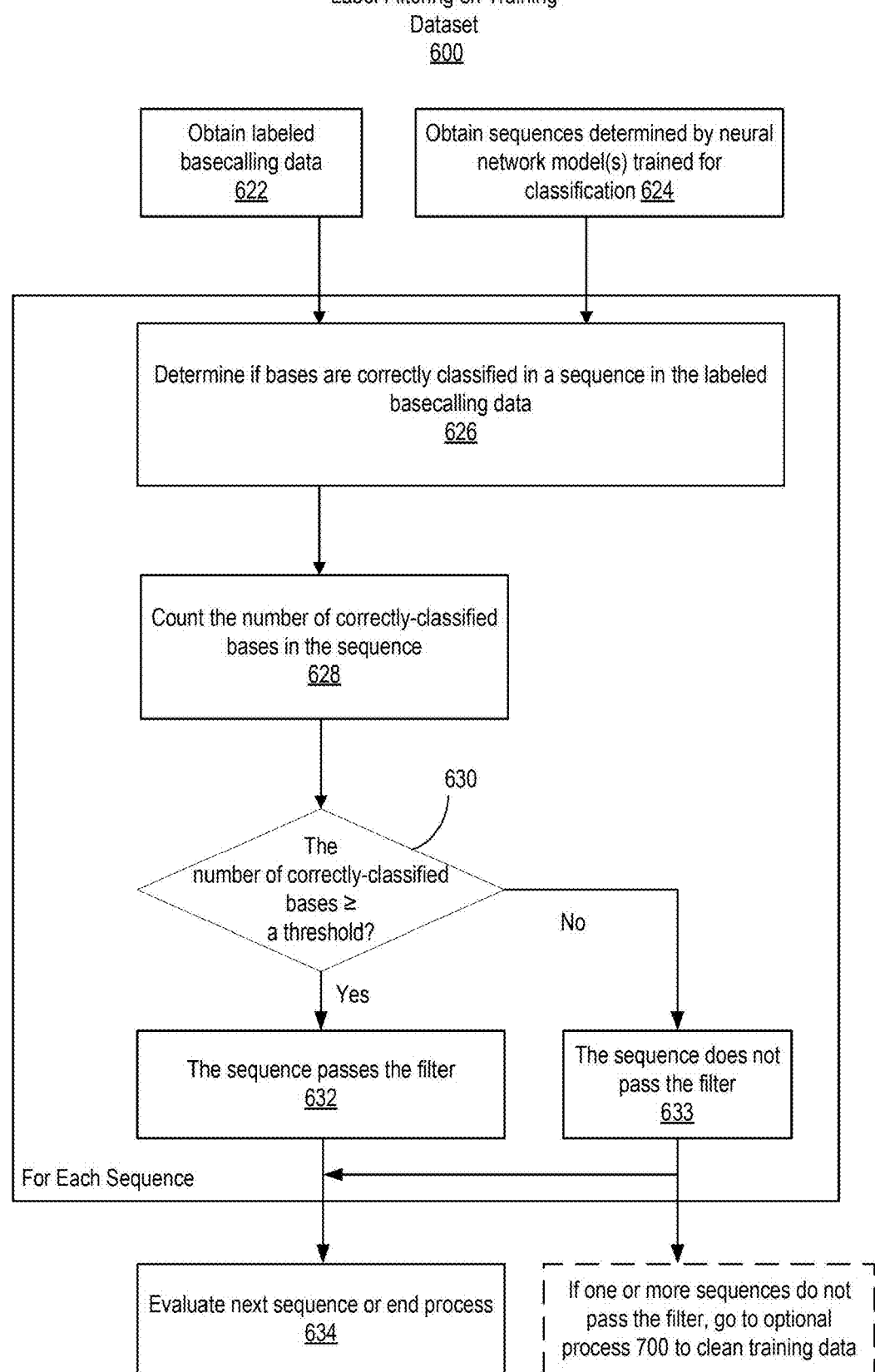

Obtain labeled
basecalling data
622

Obtain sequences determined by neural
network model(s) trained for
classification 624

Determine if bases are correctly classified in a sequence in the labeled
basecalling data
626

Count the number of correctly-classified
bases in the sequence
628

630

The
number of correctly-classified
bases ≥
a threshold?

No

Yes

The sequence passes the filter
632

The sequence does not
pass the filter
633

For Each Sequence

Evaluate next sequence or end process
634

If one or more sequences do not
pass the filter, go to optional
process 700 to clean training data

FIG. 6

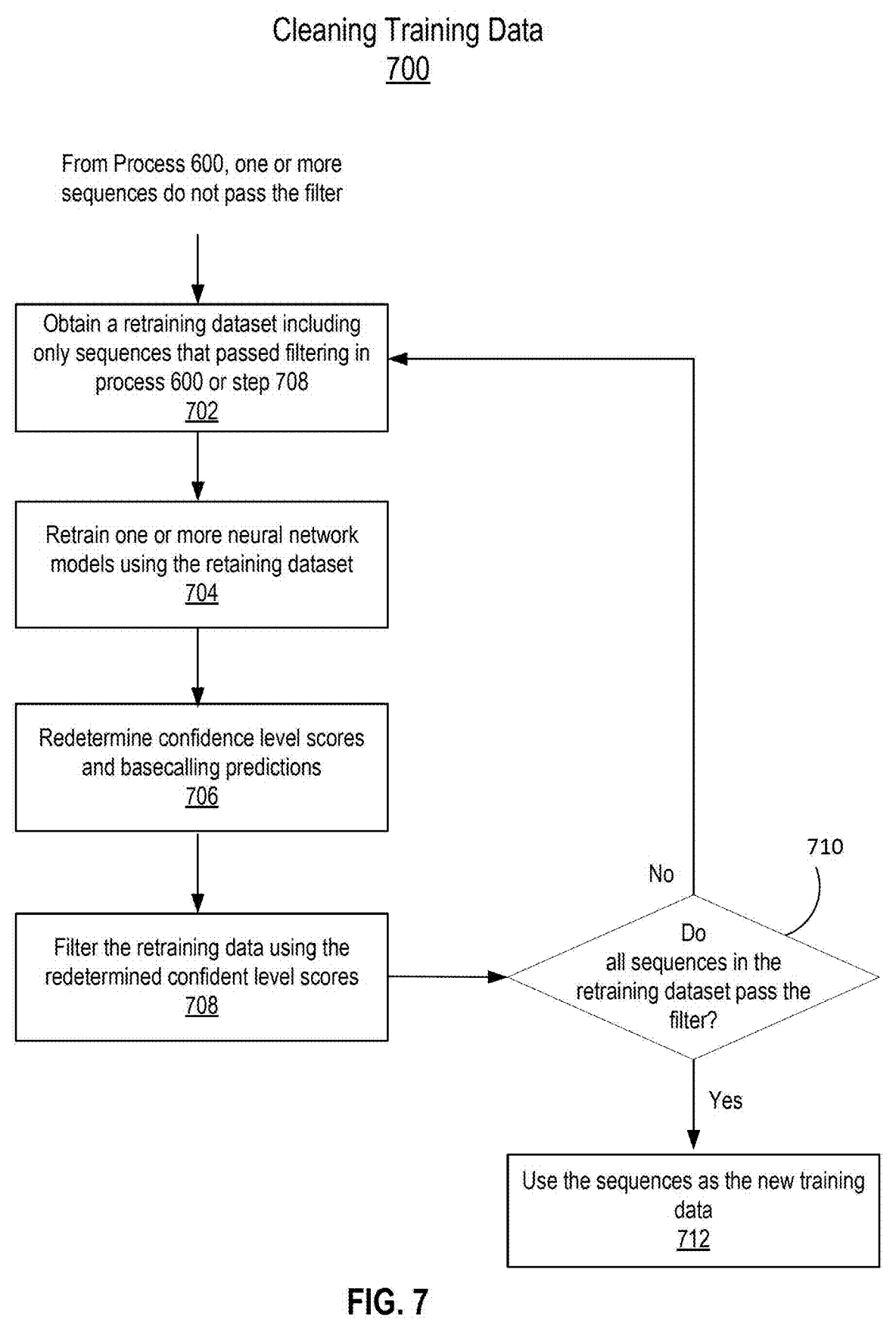

Cleaning Training Data
700

From Process 600, one or more
sequences do not pass the filter

Obtain a retraining dataset including
only sequences that passed filtering in
process 600 or step 708
702

Retrain one or more neural network
models using the retaining dataset
704

Redetermine confidence level scores
and basecalling predictions
706

Filter the retraining data using the
redetermined confident level scores
708

710

Do
all sequences in the
retraining dataset pass the
filter?

No

Yes

Use the sequences as the new training
data
712

FIG. 7

METHODS AND SYSTEMS FOR ENHANCING NUCLEIC ACID SEQUENCING QUALITY IN HIGH-THROUGHPUT SEQUENCING PROCESSES WITH MACHINE LEARNING

CROSS REFERENCE TO RELATED APPLICATIONS

This application is a continuation application of International Application Number PCT/CN2022/104105 filed on Jul. 6, 2022. The entire content of the application is hereby incorporated herein by reference for all purposes

FIELD OF TECHNOLOGY

The present disclosure relates generally to nucleic acid sequencing, and more specifically to systems, devices, and methods for enhancing quality of basecalling results obtained by high-throughput sequencing processes with machine learning.

BACKGROUND

Sequencing-by-synthesis is a method used to identify sequences of segments (also referred to as strands) of nucleic acid (e.g., DNA) molecules. Sanger sequencing is a first-generation sequencing technique that uses the sequencing-by-synthesis method. Historically, Sanger sequencing has a high degree of accuracy but is low in sequencing throughput. Second-generation sequencing techniques (also referred to as next generation sequencing or NGS techniques) massively increase the throughput of the synthesizing process by parallelizing many reactions similar to those in Sanger sequencing. Third-generation sequencing techniques allow direct sequencing of single nucleic acid molecules. In any of the sequencing technology generations, basecalling is an essential process by which an order of the nucleotide bases in a template strand is inferred during or after a sequencing readout.

When performing nucleic sequencing (e.g., DNA sequencing), fluorescently labeled dNTP and polymerase are frequently used. Under the reaction of polymerase, dNTP complements the template strand to form a new strand according to the principle of base complementarity. The added fluorescence dye is excited by absorbing light energy from the laser. The fluorescents signals are collected and analyzed to predict the sequences of the nucleic acid.

SUMMARY

Next generation sequencing techniques (and other future generation sequencing techniques) massively increase the throughput of the synthesis process and therefore generate a massive amount of data for basecalling. The processing of the massive amount of data remains challenging. For example, they may be time consuming, computationally complex, and demanding a large amount of computing resources. In addition, the current data processing techniques may not provide a satisfactory basecalling accuracy under various conditions. For instance, in an NGS process, the fluorescence signal quality decays over time, which may negatively impact the accuracy of the data processing results. Furthermore, during a sequencing process, there may be crosstalk between different fluorescence signal channels and loss of synchrony in cluster molecules (also referred to as cluster phasing and prephasing). The loss of synchrony in cluster molecules are caused by stochastic nature of chemical reactions and other factors in which some molecules may fail to incorporate a labelled nucleotide whereas some other molecules may incorporate more than one nucleotide. This results in leakage in signal intensity between cycles. The crosstalk and loss in synchrony in turn cause difficulties in predicting nucleotide bases.

Recently, machine learning models have been developed for basecalling. Machine learning techniques provide a method of self-learning by a computing device. Some existing machine learning models use, for example, a combination of convolutional neural network (CNN) and a recurrent neural network (RNN) network. The CNN is configured to perform image analysis to detect clusters of fluorescence signals and the RNN is configured to process sequence data. Other machine learning based models have also been used.

Deep learning-based basecalling approaches can provide matching or improved performance compared to traditional basecalling approaches, while enabling high-throughput basecalling processes. During the basecalling process, it is desired to achieve high sequencing quality such as higher overall sequencing accuracy. Exiting techniques for improving sequencing quality may filter sequences based on chastity filtering techniques, which compute the intensity ratio between the DNA signal channel having the highest intensity and the channel having the second highest intensity.

This disclosure provides an improved filtering techniques that can provide higher sequencing accuracy for processing high-throughput sequencing data. The filtering structure uses a hierarchical network structure comprising one or more network blocks for obtaining high quality sequences. Each network block comprises a base network module (or simply a base network) and a sequence filter. The base network generates one or more sequencing quality indicators. The sequencing quality indicators can represent qualities of accuracy of the basecalling of individual bases in a sequence, the quality of one or more sequences individually, or the quality of a group of sequences as a whole. The sequence filter generates the filtered results based on the various filtering strategies based on the one or more sequencing quality indicators.

Embodiments of the present invention provide a computer-implemented method for enhancing quality of basecalling results obtained by a high-throughput process for sequencing nucleic acid molecules. The method comprises obtaining input data comprising a first group of sequences of nucleic acid; determining, based on the input data and one or more neural-network based models, one or more sequencing quality indicators and/or basecalling predictions. The method further comprises filtering, using a sequence filter, the first group of sequences based on one or more of the plurality of sequencing quality indicators. The method further comprises obtaining a second group of sequences based on filtering results. The second group of sequences has higher data quality than the first group of sequences. The method further comprises providing basecalling predictions using the second group of sequences by at least one of the one or more neural network based models.

Embodiments of the present invention further provide a system for enhancing quality of basecalling results obtained by a high-throughput process for sequencing nucleic acid molecules. The system comprises one or more processors of at least one computing device; and a memory storing one or more instructions, when executed by the one or more processors, cause the one or more processors to perform steps including obtaining input data for performing basecalling; and determining, based on the input data and one or more neural-network based models trained for basecalling, one or more sequencing quality indicators and a first group of sequences of nucleic acid. The instructions further cause the one or more processors to perform steps including filtering, using a sequence filter, the first group of sequences based on one or more of the plurality of sequencing quality indicators; and obtaining a second group of sequences based on filtering results. The second group of sequences has higher data quality than the first group of sequences. The instructions further cause the one or more processors to perform steps including providing basecalling prediction using the second group of sequence by at least one of the one or more neural network based models.

Embodiments of the present invention further provide a non-transitory computer readable medium comprising a memory storing one or more instructions which, when executed by one or more processors of at least one computing device, cause the at least one computing device to perform a method for enhancing quality of basecalling results obtained by a high-throughput process for sequencing nucleic acid molecules. The method comprises obtaining input data comprising a first group of sequences of nucleic acid; determining, based on the input data and one or more neural-network based models, one or more sequencing quality indicators and/or basecalling predictions. The method further comprises filtering, using a sequence filter, the first group of sequences based on one or more of the plurality of sequencing quality indicators. The method further comprises obtaining a second group of sequences based on filtering results. The second group of sequences has higher data quality than the first group of sequences. The method further comprises providing basecalling predictions using the second group of sequences by at least one of the one or more neural network based models.

These and other embodiments are described more fully below.

BRIEF DESCRIPTION OF THE DRAWINGS

FIG. 3 is a flowchart illustrating a method for enhancing quality of basecalling results obtained by a high-throughput process for sequencing nucleic acid molecules in accordance with an embodiment of the present invention;

FIG. 5A is a flowchart illustrating a method for performing basecalling quality filtering (BCQF) in accordance with an embodiment of the present invention;

FIG. 5B is a flowchart illustrating a method for performing sequence quality filtering in accordance with an embodiment of the present invention;

FIG. 6 is a flowchart illustrating a method of training dataset label filtering in accordance with an embodiment of the present invention;

FIG. 7 is a flowchart illustrating a method of cleaning a training dataset in accordance with an embodiment of the present invention;

Figure 1:
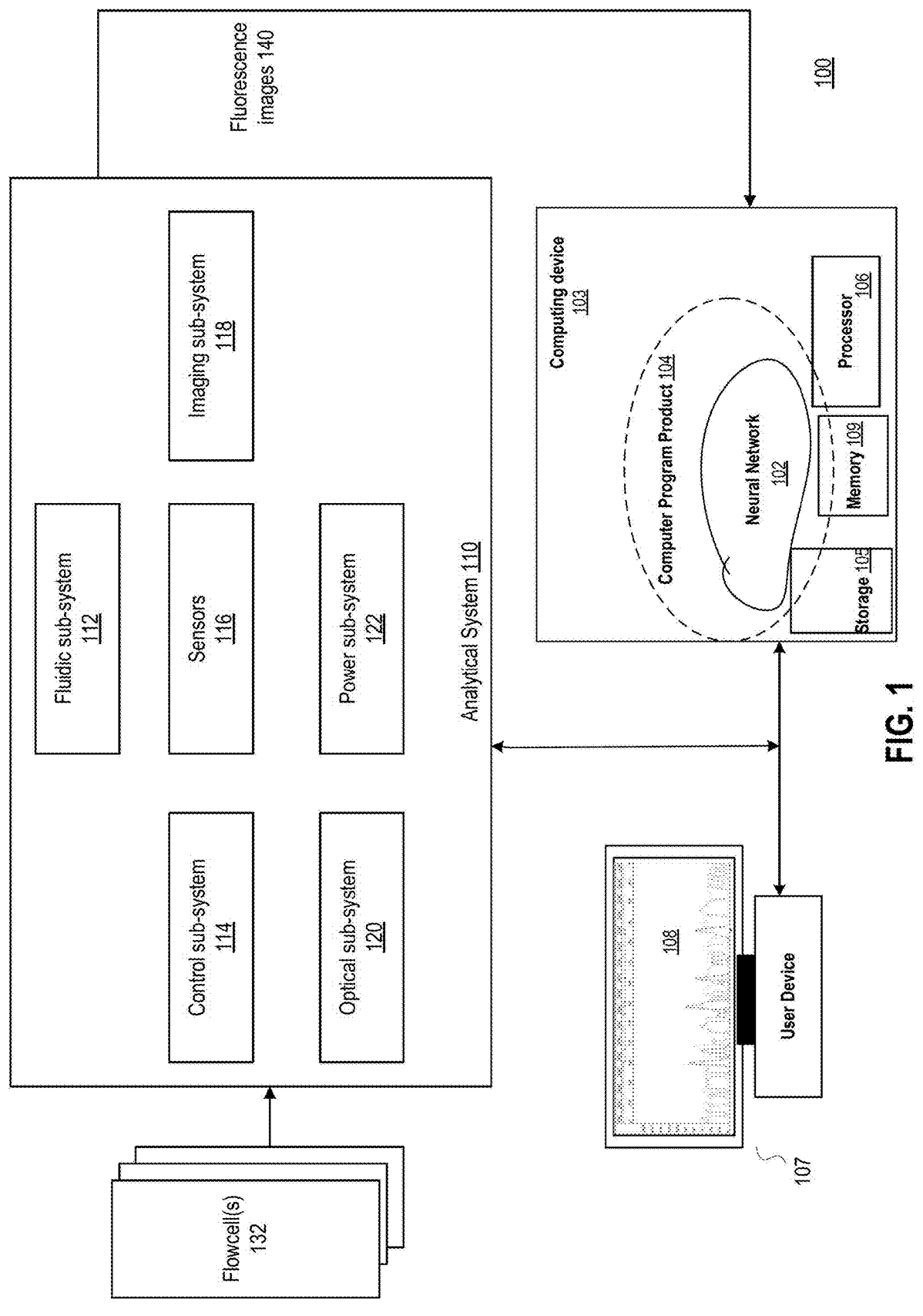
FIG. 1 illustrates an exemplary next generation sequencing (NGS) system in accordance with an embodiment of the present invention.

While the embodiments of the present invention are described with reference to the above drawings, the drawings are intended to be illustrative, and other embodiments are consistent with the spirit, and within the scope, of the invention.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

As described above, next generation sequencing techniques (and other future generation sequencing techniques) massively increase the throughput of the synthesis process and therefore generate a massive amount of data for basecalling. Accurately analyzing and processing the mass fluorescence signals remain challenging, at least partially because the fluorescence signal quality decays over time. For example, it may be difficult to mitigate or eliminate crosstalk and/or cluster phasing when predicting the DNA bases in a sequence.

Machine learning provides techniques that allow a computing device to make predictions without being explicitly programmed and enable the computing device to study the features of the data. Traditional machine learning systems are developed such that users need to manually design features and choose classifiers. With the rapid development of deep learning, the emergence of deep neural network has made end-to-end learning possible, thereby reducing or eliminating the effort of manual programming and feature selecting by a user. Deep learning technologies are being developed rapidly. Convolutional Neural Network (ConvNet/CNN) is a deep learning algorithm that is frequently used for image analysis. The Recurrent Neural Network (RNN) is frequently used to process sequence data. Due to their wide applicability and enhanced prediction ability, CNN and RNN have great potential in bioinformatics research.

In DNA sequencing, a statistical model such as the AYB (All Your Base) model has been proposed to produce more accurate basecalling results. Recently, the neural network-based basecalling models such as RNN base models, CNN based models, and a combination of transformer and CNN based model have been proposed. Deep learning-based basecalling approaches can provide matching or improved performance compared to traditional basecalling approaches, while enable high-throughput basecalling processes. During the basecalling process, it is desired to achieve high sequencing quality such as high overall sequencing accuracy. Improving the DNA sequencing accuracy can be achieved from several aspects including, for example, improving the efficiency of biochemical reagents, improving the quality of the optical system, and/or improving the basecalling algorithms.

This disclosure provides methods and systems for improving basecalling algorithms by filtering an initial group of sequences to obtain a high-quality group of sequences. Existing techniques for filtering sequences to exclude low quality sequencing data use chastity filtering, which computes the intensity ratio between the DNA signal channel having the highest intensity and the channel having the second highest intensity. The intensity ratio represents the cluster quality. The chastity filtering method requires corrections of the data crosstalk and cluster phasing. As a result, the quality of the crosstalk and cluster phasing corrections limit the filtering performance. Furthermore, there is usually a limit to obtain a higher quality sequencing result with a single deep learning network. Therefore, a more effective method for improving the sequence quality without the limitations described above is desired.

Embodiments of the present invention are discussed herein. In some embodiments, a hierarchical processing network structure for basecalling is provided. The network structure uses one or more network blocks for obtaining high quality sequences. Each network block comprises a base network and a sequence filter. The base network generates one or more sequencing quality indicators such as sequence quality filtering via network (SQFN) passing indices, a sequence dataset quality index, basecalling confidence level scores, etc. The sequencing quality indicators can represent the accuracy of basecalling of individual bases in a sequence, the qualities of one or more sequences individually, and the quality of a group of sequences as a whole. The sequence filter generates the filtered results based on pre-configured filtering strategies. Such filtering strategies may include basecalling quality filtering (BCQF) and passing indices synthetization (e.g., a logic AND operation). In some embodiments, the filtered results obtained by one network block can be provided to another network block for further processing. For instance, multiple network blocks can be used in a hierarchical processing network structure to measure the DNA sequence signal quality to exclude the low-quality signals that are prone to be misidentified, thereby improving the final DNA sequencing quality. Details of the embodiments of the present invention are described below.

Next Generation (and Future Generations) Sequencing System

FIG. 1 is a block diagram illustrating an exemplary analytical system 110. As illustrated in FIG. 1, analytical system 110 includes an optical sub-system 120, an imaging sub-system 118, a fluidic sub-system 112, a control sub-system 114, sensors 116, and a power sub-system 122. Analytical system 110 can be used to perform next-generation sequencing (NGS) reactions and produce fluorescence images 140 captured during multiple synthesis cycles. These images 140 are provided to computer(s) 103 for basecalling.

Figure 2:
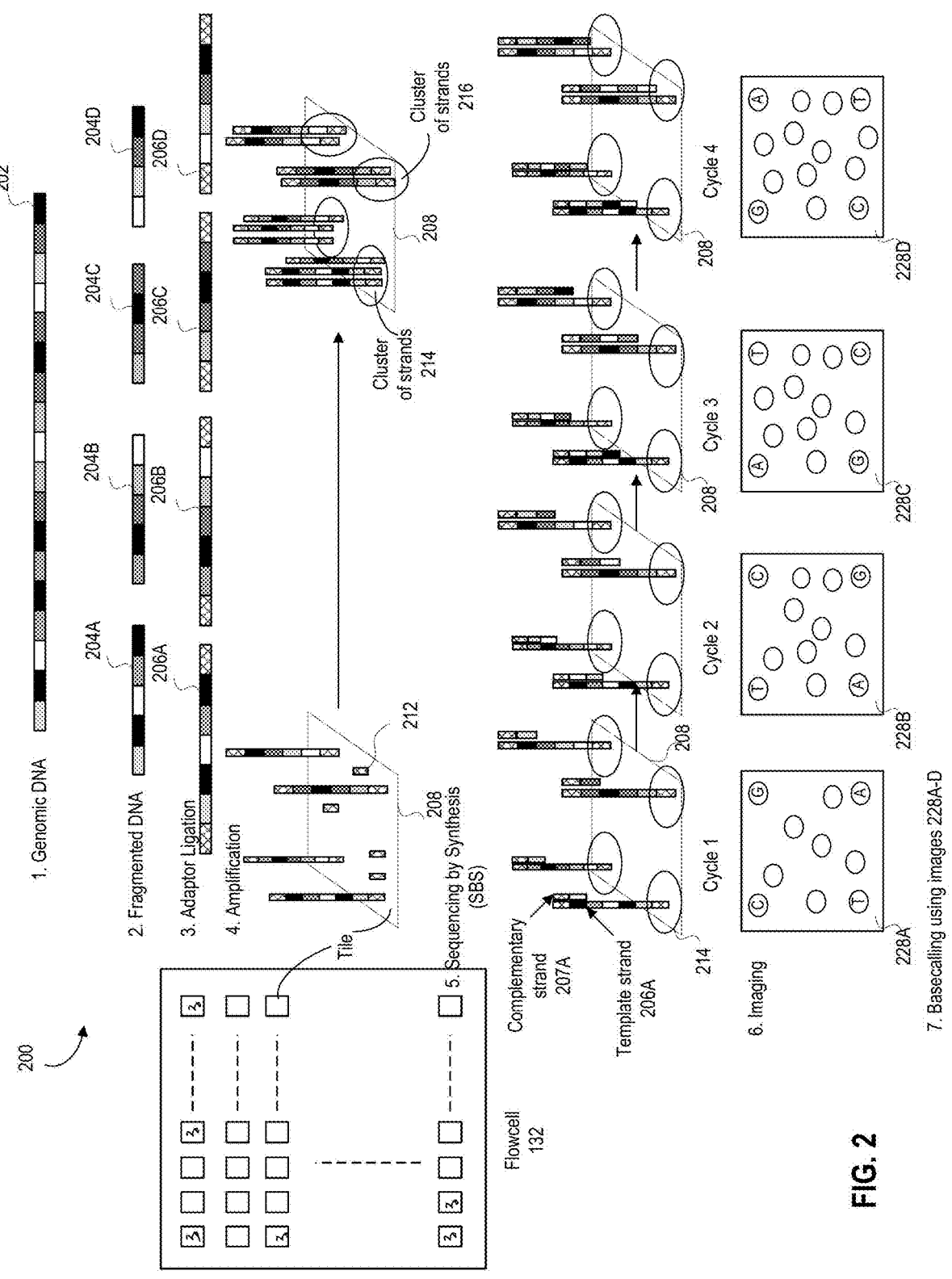
FIG. 2 illustrates an exemplary sequencing-by-synthesis process using an NGS system in accordance with an embodiment of the present invention.

Referencing FIG. 1, one or more flowcell(s) 132 are provided to analytical system 110. A flowcell is a slide with fluidic channels or lanes, where the sequencing reactions occur. In some embodiments, each fluidic channel of a flowcell includes an array of tiles. Each tile may have numerous clusters generated on the surface and forms a logical unit for imaging and data processing. FIG. 2 illustrates a flowcell 132 having multiple tiles and also illustrates an exemplary tile 208. The synthesis process occurs in flowcell 132 and is described below in more detail.

Referencing FIG. 1, optical sub-system 120, imaging sub-system 118, and sensors 116 are configured to perform various functions including providing an excitation light, guiding or directing the excitation light (e.g., using an optical waveguide), detecting light emitted from samples as a result of the excitation light, and converting photons of the detected light to electrical signals. For example, optical sub-system 120 includes an excitation optical module and one or more light sources, an optical waveguide, and/or one or more filters. In some embodiments, the excitation optical module and the light source(s) include laser(s) and/or light-emitting diode (LED) based light source(s) that generate and emit excitation light. The excitation light can have a single wavelength, a plurality of wavelengths, or a wavelength range (e.g., wavelengths between 200 nm to 1600 nm). For instance, if system 110 has a four-fluorescence channel configuration, optical sub-system 120 uses four different fluorescent lights having different wavelengths to excite four different corresponding fluorescent dyes (one for each of the bases A, G, T, C).

In some embodiments, the excitation optical module can include further optical components such as beam shaping optics to form uniform collimated light. The excitation optical module can be optically coupled to an optical waveguide. For example, one or more of grating(s), mirror(s), prism(s), diffuser(s), and other optical coupling devices can be used to direct the excitation lights from the excitation optical module toward the optical waveguide.

In some embodiments, the optical waveguide can include three parts or three layers—a first light-guiding layer, a fluidic reaction channel, and a second light-guiding layer. The fluidic reaction channel may be bounded by the first light-guiding layer on one side (e.g., the top side) and bounded by the second light-guiding layer on the other side (e.g., the bottom side). The fluidic reaction channel can be used to dispose flowcell(s) 132 bearing the biological sample. The fluidic reaction channel can be coupled to, for example, fluidic pipelines in fluidic sub-system 112 to receive and/or exchange liquid reagent. A fluidic reaction channel can be further coupled to other fluidic pipelines to deliver liquid reagent to the next fluidic reaction channel or a pump/waste container.

In some embodiments, the fluorescent lights are delivered to flowcell(s) 132 without using an optical waveguide. For example, the fluorescent lights can be directed from the excitation optical module to flowcell(s) 132 using free-space optical components such as lens, grating(s), mirror(s), prism(s), diffuser(s), and other optical coupling devices.

As described above, fluidic sub-system 112 delivers reagents to flowcell(s) 132 directly or through a fluidic reaction channel using fluidic pipelines. Fluidic sub-system 112 performs reagent exchange or mixing, and dispose waste generated from the liquid photonic system. One embodiment of fluidic sub-system 112 is a microfluidics sub-system, which can process small amount of fluidics using channels measuring from tens to hundreds of micrometers. A microfluidics sub-system allows accelerating PCR processes, reducing reagent consumption, reaching high throughput assays, and integrating pre- or post-PCR assays on-chip. In some embodiments, fluidic sub-system 112 can include one or more reagents, one or more multi-port rotary valves, one or more pumps, and one or more waste containers.

The one or more reagents can be sequencing reagents in which sequencing samples are disposed. Different reagents can include the same or different chemicals or solutions (e.g., nucleic acid primers) for analyzing different samples. Biological samples that can be analyzed using the systems described in this application include, for example, fluorescent or fluorescently-labeled biomolecules such as nucleic acids, nucleotides, deoxyribonucleic acid (DNA), ribonucleic acid (RNA), peptide, or proteins. In some embodiments, fluorescent or fluorescently-labeled biomolecules include fluorescent markers capable of emitting light in one, two, three, or four wavelength ranges (e.g., emitting red and yellow lights) when the biomolecules are provided with an excitation light. The emitted light can be further processed (e.g., filtered) before they reach the image sensors.

With reference to FIG. 1, analytical system 110 further includes a control sub-system 114 and a power sub-system 122. Control sub-system 114 can be configured (e.g., via software) to control various aspects of the analytical system 110. For example, control sub-system 114 can include hardware and software to control the operation of optical sub-system 120 (e.g., control the excitation light generation), fluidic sub-system 112 (e.g., control the multi-port rotary valve and pump), and power sub-system 122 (e.g., control the power supply of the various systems shown in FIG. 1). It is understood that various sub-systems of analytical system 110 shown in FIG. 1 are for illustration only. Analytical system 110 can include more or fewer sub-systems than shown in FIG. 1. Moreover, one or more sub-systems included in analytical system 110 can be combined, integrated, or divided in any manner that is desired.

Referencing FIG. 1, analytical system 110 includes sensor(s) 116 and an imaging sub-system 118. Sensor(s) 116 detect photons of light emitted from the biological sample and convert the photons to electrical signals. Sensor(s) 116 are also referred to as image sensor(s). An image sensor can be a semiconductor-based image sensor (e.g., silicon-based CMOS sensor) or a charge-coupled device (CCD) image sensor. A semiconductor-based image sensor can be a backside illumination (BSI) based image sensor or a front side illumination (FSI) based image sensor. In some embodiments, sensor(s) 116 may include one or more filters to remove scattered light or leakage light while allowing a substantial portion of the light emitted from the biological sample to pass. Filters can thus improve an image sensor's signal-to-noise ratio.

The photons detected by sensor(s) 116 are processed by imaging sub-system 118. An imaging sub-system 118 includes a signal processing circuitry, which is electrically coupled to sensor(s) 116 to receive electrical signals generated by sensor(s) 116. In some embodiments, the signal processing circuitry can include one or more charge storage elements, an analog signal readout circuitry, and a digital control circuitry. In some embodiments, the charge storage elements receive or read out electrical signals generated in parallel based on substantially all photosensitive elements of an image sensor 116 (e.g., using a global shutter); and transmit the electrical signals to the analog signal read-out circuitry. The analog signal read-out circuitry may include, for example, an analog-to-digital converter (ADC), which converts analog electrical signals to digital signals.

In some embodiments, after the signal processing circuitry of imaging sub-system 118 converts analog electrical signals to digital signals, it can transmit the digital signals to a data processing system to produce digital images such as fluorescence images 140. For example, the data processing system can perform various digital signal processing (DSP) algorithms (e.g., compression) for high-speed data processing. In some embodiments, at least part of the data processing system can be integrated with the signal processing circuitry on a same semiconductor die or chip. In some embodiments, at least part of the data processing system can be implemented separately from the signal processing circuitry (e.g., using a separate DSP chip or cloud computing resources). Thus, data can be processed and shared efficiently to improve the performance of the sample analytical system 110. It is appreciated that at least a portion of the signal processing circuitry and data processing system in imaging sub-system 118 can be implemented using, for example, CMOS-based application specific integrated circuits (ASIC), field programmable gate array (FPGA), discrete IC technologies, and/or any other desired circuit techniques.

It is further appreciated that power sub-system 122, optical sub-system 120, imaging sub-system 118, sensor(s) 116, control sub-system 114, and fluidic sub-system 112 may be separate systems or components or may be integrated with one another. The combination of at least a portion of optical sub-system 120, imaging sub-system 118, and sensors 116 is sometimes also referred to as a liquid photonic system.

Referencing FIG. 1, analytical system 110 provides fluorescence images 140 and/or other data to a computing device 103 to perform further processes including image preprocessing, cluster detection, feature extraction, and basecalling. Instructions for implementing one or more deep learning neural networks 102 reside on computing device 103 in computer program product 104 which is stored in storage 105 and those instructions are executable by processor 106. One or more deep learning neural networks 102 can be used for performing various processes described below. When processor 106 is executing the instructions of computer program product 104, the instructions, or a portion thereof, are typically loaded into working memory 109 from which the instructions are readily accessed by processor 106. In one embodiment, computer program product 104 is stored in storage 105 or another non-transitory computer readable medium (which may include being distributed across media on different devices and different locations). In alternative embodiments, the storage medium is transitory.

In one embodiment, processor 106 in fact comprises multiple processors which may comprise additional working memories (additional processors and memories not individually illustrated) including a graphics processing unit (GPU) comprising at least thousands of arithmetic logic units supporting parallel computations on a large scale. Other embodiments comprise one or more specialized processing units comprising systolic arrays and/or other hardware arrangements that support efficient parallel processing. In some embodiments, such specialized hardware works in conjunction with a CPU and/or GPU to carry out the various processing described herein. In some embodiments, such specialized hardware comprises application specific integrated circuits and the like (which may refer to a portion of an integrated circuit that is application-specific), field programmable gate arrays and the like, or combinations thereof. In some embodiments, however, a processor such as processor 106 may be implemented as one or more general purpose processors (preferably having multiple cores) without necessarily departing from the spirit and scope of the present invention.

User device 107 incudes a display 108 for displaying results of processing carried out by the one or more deep learning neural networks 102. In alternative embodiments, a neural network such as neural network 102, or a portion of it, may be stored in storage devices and executed by one or more processors residing on analytical system 110 and/or user device 107. Such alternatives do not depart from the scope of the invention.

Sequencing-by-Synthesis

FIG. 2 illustrates an exemplary sequencing-by-synthesis process 200 using an analytical system (e.g., system 110) in accordance with an embodiment of the present invention. In step 1 of process 200, the analytical system heats up a biological sample to break apart the two strands of a DNA molecule. One of the single strands will be used as the DNA template strand. FIG. 2 illustrates such a DNA template strand 202, which can be a genomic DNA. Template strand 202 may be a strand that includes a sequence of nucleotide bases (e.g., a long sequence having few hundreds or thousands of bases). It is understood that there may be many such templated strands generated from using the polymerase chain reaction (PCR) techniques. It is further understood that there may also be other isolation and purification processes applied to the biological sample to obtain the DNA template strands.

In step 2 of process 200, the analytical system generates many DNA fragments from the DNA template strand 202. These DNA fragments, such as fragments 204A-D shown in FIG. 2, are smaller pieces containing fewer number of nucleotide bases. These DNA fragments can thus be sequenced in a massively parallel manner to increase the throughput of the sequencing process. Step 3 of process 200 performs adapter ligation. Adapters are oligonucleotides with sequences that are complementary to the priming oligos disposed on the flowcell(s). The ends of the nucleic acid fragments are ligated with adapters to obtain ligated DNA fragments (e.g., 206A-D) to enable the subsequent sequencing process.

The DNA fragmentation and adapter ligation steps prepare the nucleic acids to be sequenced. These prepared, ready-to-sequence samples are referred to as "libraries" because they represent a collection of molecules that are sequenceable. After the DNA fragmentation and adapter ligation steps, the analytical system generates a sequencing library representing a collection of DNA fragments with adapters attached to their ends. In some embodiments, prepared libraries are also quantified (and normalized if needed) so that an optimal concentration of molecules to be sequenced is loaded to the system. In some embodiments, other processes may also be performed in the library preparation process. Such processes may include size selection, library amplification by PCR, and/or target enrichment.

After library preparation, process 200 proceeds to step 4 for clonal amplification to generate clusters of DNA fragment strands (also referred to as template strands). In this step, each of the DNA fragments is amplified or cloned to generate thousands of identical copies. These copies form clusters so that fluorescence signals of the clusters in the subsequent sequencing reaction are strong enough to be detected by the analytical system. One such amplification process is known as bridge amplification. In a bridge amplification process, a tile (e.g., tile 208 in FIG. 2) is used and priming oligos are disposed on the tile. Each DNA fragment in the library anneals to the primer oligo disposed on the tile via the adapters attached to the DNA fragment. The complementary strand of a ligated DNA fragment is then synthesized. The complementary strand folds over and anneals with the other type of primer oligo disposed on the tile. A double-stranded bridge is thus formed after synthesis of the complementary strand.

The double-stranded bridge is denatured, forming two single strands attached to the tile. This process of bridge amplification repeats many times. The double-stranded clonal bridges are denatured, the reverse strands are removed, and the forward strands remain as clusters for subsequent sequencing. Two such clusters of strands are shown as clusters 214 and 216 in FIG. 2. Many clusters having different DNA fragments can be attached to a tile. For example, cluster 214 may be a cluster of ligated fragmented DNA 206A disposed on tile 208; and cluster 216 may be a cluster of ligated fragmented DNA 206B also disposed on tile 208. The subsequent sequencing can be performed in parallel to some or all of these different clusters disposed on a tile and in turn, some or all the clusters disposed on many tiles of the flowcell(s). The sequencing process can thus be massively parallel.

Referencing FIG. 2, after the clonal amplification in step 4, process 200 proceeds to step 5, where the clusters are sequenced by synthesis (SBS). In this SBS step, nucleotides are incorporated by a DNA polymerase into the complementary DNA strands of the clonal clusters of the DNA fragments one base at a time in each synthesis cycle. For example, as shown in FIG. 2, if cycle 1 is a beginning cycle, a first complementary nucleotide base is incorporated to the complementary DNA strand of each strand in cluster 214. FIG. 2 only shows one strand in cluster 214 for simplicity. But it is understood that similar processes can occur to some or all other strands of cluster 214, some or all other clusters on tile 208, some or all other tiles, and some or all other flowcells. This synthesis process repeats in cycle 2, where a second complementary nucleotide base is incorporated to the complementary DNA strand. This synthesis process then repeats in cycles 3, 4, and so on, until complementary nucleotide bases are incorporated for all bases in the template strand 206A or until a predetermined number of cycles is reached. Thus, if the template strand 206A has "n" nucleotide bases, there may be "n" cycles or a predetermined number of cycles (less than "n") for the entire sequencing-by-synthesis process. The complementary strand 207A is at least partially completed after all the synthesis cycles. In some embodiments, this synthesis process can be performed for some or all strands, clusters, tiles, and flowcells in parallel.

Step 6 of process 200 is an imaging step that can be performed after step 5 or in parallel with step 5. As one example, a flowcell can be imaged after the sequencing-by-synthesis process is completed for the flowcell. As another example, a flowcell can be imaged while the sequencing-by-synthesis process is being performed on another flowcell, thereby increasing the throughput. Referencing FIG. 2, in each cycle, the analytical system captures one or more images of the tile (e.g., images 228A-D) of a flowcell. The images represent the fluorescence signals detected in the particular cycle for all the clusters disposed on the tile. In some embodiments, the analytical system can have a four-channel configuration, where four different fluorescent dyes are used for identifying the four nucleotide bases. For example, the four fluorescence channels use different types of dyes for generating fluorescent signals having different spectral wavelengths. Different dyes may each bind with a different target and produce signals with a different fluorescence color or spectrum. Examples of the different dyes may include a Carboxyfluorescein (FAM) based dye that produces signals having a blue fluorescence color, a Hexachloro-fluorescein (HEX) based dye that produces signals having a green fluorescence color, a 6-carboxy-X-rhodamine (ROX) based dye that produces signals having a red fluorescence color, a Tetramethylrhodamine (TAMRA) based dye that produces signals having a yellow fluorescence color.

In a four-channel configuration, the analytical system captures an image of the same tile for each channel. Therefore, for each tile, the analytical system produces four images in each cycle. This imaging process can be performed with respect to some or all the tiles and flowcells, producing a massive number of images in each cycle. These images represent the fluorescence signals detected in that particular cycle for all the clusters disposed on the tile. The images captured for all cycles can be used for basecalling to determine the sequences of the DNA fragments. A sequence of an DNA fragment includes an ordered combination of nucleotide bases having four different types, i.e., Adenine (A), Thymine (T), Cytosine (C), and Guanine (G). The sequences of multiple DNA fragments can be integrated or combined to generate the sequence of the original genomic DNA strand. Embodiments of this invention described below can process the massive numbers of images in an efficient way and perform basecalling using improved architectures of deep learning neural networks. The basecalling process according to the embodiments of this invention thus has a faster speed and a lower error rate. While the above descriptions use DNA as an example, it is understood that the same or similar processes can be used for other nucleic acid, such as RNA and artificial nucleic acid.

FIG. 3 is a flowchart illustrating a method 300 for enhancing the quality of basecalling results obtained by a high-throughput process for sequencing nucleic acid molecules in accordance with an embodiment of the present invention. Method 300 can be performed by one or more computing devices such as device 103. Method 300 may begin with step 302, which obtains input data for a hierarchical processing network structure. The input data includes an initial group (e.g., a first group) of sequences of nucleic acid (e.g., DNA sequences signals). The initial group of sequences may represent unknown nucleic acid sequences and are sometimes represented by input embedding vectors. The initial group of sequences can be obtained based on image preprocessing and cluster detection, or by any other desired sequencing detection methods. In some embodiments, image preprocessing processes images of fluorescence signals captured by an analytical system in multiple synthesis cycles. Processing the images before performing the subsequent steps of cluster detection and the basecalling processes improves the accuracy of cluster detection, reduces signal interference between close-by clusters, and improves the accuracy of basecalling. Image preprocessing may include, for example, light correction, image registration, image normalization, image enhancements, etc.

Cluster detection uses the preprocessed image to detect center positions of clusters of fluorescence signals (or simply cluster detection). In some embodiments, cluster detection can use a trained CNN to generate an output feature map and use a local Maxima algorithm to determine the center positions of the clusters. The extracted cluster information can be represented in embedding vectors used for basecalling. The embedding vectors represent unknown nucleic acid sequences. Embodiments of the image prepressing and cluster detection methods are described in more detail in International Application No. PCT/CN2021/141269, entitled "DEEP LEARNING BASED METHODS AND SYSTEMS FOR NUCLEIC ACID SEQUENCING", filed Dec. 24, 2021, the content of which is incorporated hereby in reference in its entirety for all purposes.

With reference back to FIG. 3, step 304 determines, using one or more neural network-based models, one or more sequencing quality indicators and/or one or more basecalling predications. In some embodiments, the basecalling predications are outputted at step 310 after filtering is performed. The one or more neural network-based models may include an RNN-based deep learning model, a transformer-based deep learning model, a one-dimensional convolution based deep learning model, and/or any other desired machine learning or deep learning based models for basecalling. Some of the models are described in more detail in in International Application No. PCT/CN2021/141269. Basecalling predictions represent the prediction of the bases in a sequence by using the one or more neural-network based models. The basecalling results include predicted nucleic acid sequences (e.g., DNA fragments). In some embodiments, the neural network-based models can produce basecalling predictions for all clusters of fluorescence signals captured in the images in "n" cycles in parallel. This greatly reduces the processing time for basecalling.

Using these deep learning models for basecalling, one or more sequencing quality indicators can be determined in addition to the basecalling predictions. The sequencing quality indicators comprises at least one of sequence quality filtering network (SQFN) passing indices, a dataset quality index, and confidence level scores. These sequencing quality indicators are described in more detail below.

With reference still to FIG. 3, in step 306, a sequence filter filters the first group of sequences based on one or more of the sequencing quality indicators. In step 308, based on the filtering results, a second group of sequences are obtained. The second group of sequences have higher data quality than the first group of sequences. For example, compared to the first group of sequences, sequences in the second group of sequences may generally have higher accuracy as to the base prediction. In the second group of sequences, the number of sequences that have higher basecalling accuracy may be greater than that in the first group sequences. The overall dataset quality of the second group of sequences can thus be higher than the first group of sequences. As such, the second group of sequences has a higher data quality, individually or as a group, than the first group of sequences. Higher quality is generally desired for the high throughput next generation sequencing techniques. In some embodiments, with filtering, the quality of the sequences obtained by using a high throughput sequencing process can match or even surpass the quality of sequences obtained by using low-throughput traditional sequencing techniques. In some embodiments, step 310 outputs the basecalling predictions of the second group of sequences. The second group of sequences has a higher quality than the first group of sequences. Therefore, the basecalling may be performed using the second group of sequences and the basecalling predictions are outputted.

Figure 4:
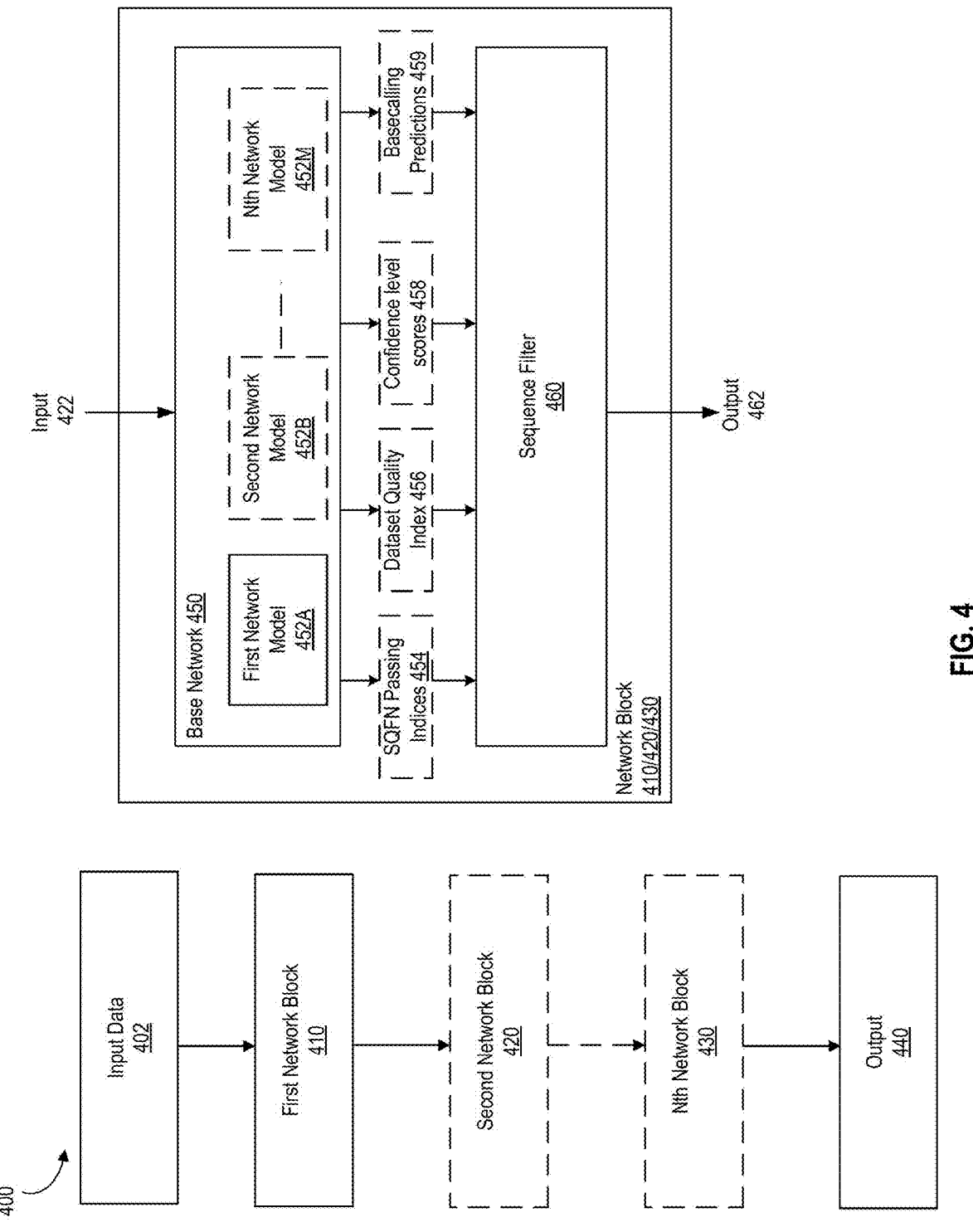
FIG. 4 is a block diagram illustrating a hierarchical processing network structure for basecalling using one or more network blocks in accordance with an embodiment of the present invention.

FIG. 4 is a block diagram illustrating a hierarchical processing network structure 400 for basecalling using one or more network blocks in accordance with an embodiment of the present invention. Network structure 400 receives input data 402. As described above, input data 402 include a first group of sequences of nucleic acid (e.g., DNA sequences). The first group of sequences may represent unknown nucleic acid sequences, bases of which have not been predicted. The first group of sequences is sometimes represented by input embedding vectors.

As shown in FIG. 4, network structure 400 comprises one or more network blocks including, for example, first network block 410 and optionally second network block 420, third network block (not shown), and so forth. In general, network structure may have N network blocks (e.g., up to Nth network block 430), where N is a number that is greater than 1. FIG. 4 also illustrates an embodiment of a single network block (e.g., network block 410, 420, or 430). A network block comprises a base network 450 and a sequence filter 460. Base network 450 can include one or more network models such as first network model 452A and optionally second network model 452B, third network model (not shown), and so forth. In general, base network 450 may include M network models, where M is a number that is greater than 1. Each of the network models 452A-M included in base network 450 can include, for example, a MLP, CNN, RNN-based deep learning network, a transformer-based deep learning network, a 1-dimensional CNN, and/or any other desired neural network models that can process sequence data.

If multiple network models are included in a base network 450, parallel processing of input data 402 can be performed, thereby increasing the performance of base network 450. Furthermore, in some embodiments, multiple base networks may also be used, thereby further improving the quality of the result. The network models used in base network 450 may or may not be the same. For example, first network model 452A-M may use the same type of network models (e.g., all use RNN-based deep learning network model) or use different types of network models (e.g., first network model 452A uses an RNN-based deep learning network model, second network model 452B uses a transformer-based deep learning network model, etc.).

The one or more network models 452A-M in base network 450 can generate one or more sequencing quality indicators as intermedium outputs. The sequencing quality indicators include, for example, SQFN passing indices 454, dataset quality indices 456, and/or confidence level scores 458. In some embodiments, base network 450 also provide basecalling predictions 459, which include base predictions. The confidence level scores 458 comprises a plurality of confidence level scores associated with basecalling predictions. A confidence level score of a base prediction represents the degree of certainty that the base network 450 has with respect to the basecalling prediction. For example, the confidence level scores may represent 99%, 90%, 80%, etc. confidence levels. In general, a high quality base signal has a high confidence level score (e.g., 95% or higher). In some embodiments, a confidence level score can be utilized as a reference index to measure the quality of the base prediction. Based on a confidence level score, whether the base prediction is a high quality prediction (or simply whether the base is a high-quality base) can be determined. For instance, for each base prediction, its confidence level score can be compared to a confidence level threshold. If the confidence level score is greater than or equal to the confidence level threshold, the base prediction can be classified as a high quality base prediction (or simply the base can be classified as a high-quality base). The confidence level threshold can be a fixed threshold number or an adaptive threshold number, as described in more detail below.

As described in more detail below, based on the number of high-quality bases (or high quality base predictions) in a sequence, whether the sequence is a high quality sequence can be determined. In one example, the number of high-quality bases is compared to a threshold number of high-quality bases. If the number of high-quality bases is greater than or equal to a threshold number of high-quality bases, the sequence is classified as a high-quality sequence. Similar to the confidence level threshold, the threshold number of high-quality bases can be a fixed threshold number or an adaptive threshold number. The confidence level threshold number and the threshold number of high-quality bases can be determined based on the dataset quality index 456. For example, if the dataset quality index is 85%, the threshold numbers are determined via searching the corresponding threshold numbers in a threshold table. This table can either be a fixed table that is generated according to experiments or generated by real-time calculation. The real-time calculation computes a passing index distribution table for varied threshold value combinations to find the distribution close to the dataset quality index. In some embodiments, whether a sequence is a high-quality sequence can be determined based on the SQFN passing indices 454 generated directly by one or more of the network models 452A-M. SQFN passing indices 454 can be used to directly classify a sequence as a high-quality sequence or a low-quality sequence, as described in more detail below.

With reference still to FIG. 4, in some embodiments, when it is determined whether each sequence in a group of sequences is a high-quality sequence (either by counting the number of high-quality bases in each sequence or by directly classifying using a SQFN), a dataset quality index 456 can be determined. The dataset quality index 456 represents an overall sequencing quality of a group of sequences. It can be determined based on the number of high-quality sequences. For example, a group of sequences may include 100 sequences, of which 99 sequences are determined to be high-quality sequences, therefore, the overall dataset quality can be considered as 99%.

As shown in FIG. 4, base network 450 can also generate basecalling predictions 459. As described above, basecalling predictions identify the type of bases (e.g., A, T, C, G) in a sequence. The basecalling predictions may be generated by the first network block 410, second network block 420, Nth network block 430, or any of the network blocks in structure 400. In some embodiments, the basecalling predictions are generated by the last network block (e.g., the Nth network block 430). As described below, using the last network block to generate the basecalling predictions may reduce the amount of required computational effort because the last network block receives only the high-quality sequences, which are provided by the preceding network blocks through filtering.

With reference still to FIG. 4, one or more of the sequencing quality indicators (e.g., confidence level scores 458, SQFN passing indices 454, dataset quality index 456) can be provided to the sequence filter 460 to filter out low-quality sequences. The sequence filter 460 can have different structures and perform variously different filtering methods to obtain high-quality sequences. These structures and filtering methods are described in greater detail below.

In the hierarchical processing network structure 400, a subsequent network block receives sequences processed (e.g., filtered) by the previous network block and can further process the received sequences. As one example, first network block 410 processes the sequences received as its input data 402 and obtains high-quality sequences as its output. These high-quality sequences are passed to the second network block 420 as its input data. The second network block 420 can further process the input data and generate its output data. The output data of the second network block 420 may include sequences that are further filtered, and therefore the quality of the sequences can be further improved. In some embodiments, the second network block 420 may have different filtering thresholds (e.g., higher thresholds for confidence level scores, higher thresholds for the number of high-quality bases, etc.). As a result, the second network block 420 can further improve the overall quality of the sequences in its output data. In some embodiments, the sequences included in the output data of the second network block 420 may be the same as those in the input data received by second network block 420, even if the second network block 420 has a higher filtering thresholds. That is, it is possible that the filtering performed by the second network block 420 does not further remove any sequences (if the sequences at the input of the second network block 420 are already sufficiently high quality).

In a similar manner, the sequences in the output data generated by the second network block 420 can be passed to the next network block as its input data and the filtering process can be repeatedly performed. Therefore, the hierarchical process network structure 400 can be used to perform multiple levels of filtering to progressively identify high quality sequences. The number of levels of filtering (or the number of network blocks) can be configured in any desired manner and based on the sequencing quality requirements. The final output 440 of the hierarchical process network structure 400 thus may include high-quality sequences that have accurately-identified bases. The nucleic acid sequencing accuracy can thus be significantly improved. Moreover, as described above, multiple network structures 400 can be implemented with each structure having multiple network blocks which is suitable to run on GPU. As a result, the processing can achieve or maintain a high throughput while significantly improving the basecalling accuracy.

As described above, a sequence filter (e.g., filter 460) can perform different filtering methods. FIG. 5A is a flowchart illustrating such a method 500 for performing basecalling quality filtering (BCQF) in accordance with an embodiment of the present invention. Method 500 can be performed for each sequence based on confidence level scores received by a sequence filter (e.g., filter 460). In step 502, the sequence filter evaluates, based on a confidence level threshold, if bases included in a sequence are high-quality bases. For example, for each base prediction, its confidence level score can be compared to the confidence level threshold. If the confidence level score is greater than or equal to the confidence level threshold, the base prediction can be classified as a high-quality base prediction (or simply the base is classified as a high-quality base). The sequence filter can classify each base in a sequence (or at least some bases in a sequence) as a high-quality base or a low-quality base (or not a high quality base).

Next, in step 504, the sequence filter can count the number of high-quality bases in the sequence. In step 506, the sequence filter determines, based on the number of high-quality bases in the sequence, if the sequence is a high-quality sequence. For instance, if the number of high-quality bases is greater than or equal to a threshold number of high-quality bases, the sequence is classified as a high-quality sequence (step 508). If the sequence is classified as a high-quality sequence, it passes the sequence filter and may be provided to the next network block or included in the output data of the entire hierarchical process network structure. If the sequence is classified as a low-quality sequence (or classified as not a high-quality sequence), the sequence filter proceeds to evaluate the next sequence (step 510). If there are no more sequences to be evaluated, method 500 ends. In some embodiments, the method 500 also generates a BCQF index for each classified sequence. For example, if a sequence is classified as a high-quality sequence, method 500 may generate a BCQF index indicating "pass" and if a sequence is classified as a low-quality sequence (or classified as not a high-quality sequence), method 500 may generate a BCQF index indicating "fail".

Another filtering method is illustrated in FIG. 5B. FIG. 5B is a flowchart illustrating a method 530 for performing sequence quality filtering in accordance with an embodiment of the present invention. As shown in FIG. 5B, in step 532, the sequence filter (e.g., filter 460) obtains sequence quality filtering network (SQFN) passing indices. As described above, the SQFN passing indices can be generated directly by the one or more neural network-based models of a base network. In step 532, the sequence filter obtains the SQFN passing indices for a group of sequences. In one embodiment, the SQFN passing indices are derived based on the confidence level scores generated by the base network. For instance, if a binary classification is used by the one or more neural network-based models in the base network, the confidence level scores may be represented such as (0.9, 0.1), (0.95, 0.05), (0.99, 0.01), (0.1, 0.9), (0.2, 0.8), etc. These confidence level scores can be converted to Boolean values such as "True" or "False" or binary values such as "1" or "0". In some embodiments, the highest score of a sequence can be used to indicate whether the sequence is a "pass" or "fail" sequence. A "pass" sequence may be classified as a high-quality sequence and a "fail" sequence may be classified as a low-quality sequence (or not a high-quality sequence).

In step 534 of FIG. 5B, the sequence filter determines if the SQFN passing index for a sequence indicates "pass" or "fail". If the SQFN passing index indicates "pass", the sequence filter classifies the sequence as a high-quality sequence (step 536). If the SQFN passing index indicates "fail", the sequence filter classifies the sequence as a low-quality sequence (or not a high-quality sequence) and checks if there are any more sequences to be classified (step 538). If yes, the sequence filter repeats steps 534 and 536 to classify the next sequence. If no, the method 530 may end.

In some embodiments, the SQFN passing indices for a group of sequences may be used to determine (step 540) a dataset quality index. For instance, in the previous steps, the percentage of passed sequences in a group of sequences is an index to represent the overall dataset quality. The dataset quality index can be utilized to determine the filtering threshold number via searching a threshold table. This table can either be a fixed table that is generated according to experiments or generated by real-time calculation. The real-time calculation computes the passing index distribution table for varied threshold value combinations to find the distribution close to the dataset quality index.

It is understood that the above description of performing filtering (e.g., BCQF or sequence quality filter) are example processes. These filtering processes can be altered in any desired manner. Steps, and their order, can be added, removed, and changed while still achieving the same filtering results. As one example, while the above examples illustrate that the indices (e.g., the BCQF indices, the SQFN indices, the dataset quality index) correspond to binary classification (e.g., pass or fail, true or false, 1 or 0), the indices can be configured to have any numerical or Boolean values for indicating the quality of the bases, sequences, and/or datasets.

FIG. 6 is a flowchart illustrating a method 600 for training dataset label filtering in accordance with an embodiment of the present invention. Neural network models (e.g., models 452 in base network 450) are typically trained using labeled training data before they can be used to make basecalling predictions. As a result, the training data quality affects a neural network model's ability to make accurate predictions. Low-quality training data may mislead the fitting process during training. Filtering out the low-quality training data can thus improve the network performance. Processing the training dataset to filter out the low-quality training data can also use methods described above (e.g., methods 500 and 530).

In another embodiment, method 600 can be used to exclude low-quality training data from the training dataset. Method 600 is also referred to as a label filtering method, which is a machine-learning based sequencing filtering method. Method 600 can be applied to both training data and non-training data (e.g., real-world application data). With reference to FIG. 6, step 622 obtains labeled basecalling data and step 624 obtains sequences determined by neural network models (e.g., models 452 in base network 450) trained for classification. The labeled basecalling data and the sequences determined by the trained neural network models are cross-checked to remove erroneously labeled basecalling data. In particular, using the data obtained in steps 622 and 624, step 626 determines if bases are correctly classified in a sequence in the labeled basecalling data. Step 628 then counts the number of correctly-classified bases in the sequence. Step 630 determines if the number of correctly-classified bases in the sequence is greater than or equal to a threshold number. If yes, step 632 determines that the sequence passes the filter, indicating that the labeled basecalling data for this particular sequence in the training data is of high-quality. If no, step 633 determines that the sequence does not pass the filter, indicating that the labeled basecalling data for this particular sequence in the training data is of low-quality (or not of high-quality). The threshold number can be fixed or adaptive. The above steps 626, 628, 630, 632, and 633 can be repeated for each sequence in the training data. If a particular sequence passes the filter, the method 600 proceeds to evaluate the next sequence (step 634). If there are no more sequences to be evaluated, method 600 may end. In some embodiments, if one or more sequences do not pass the filter, indicating that the training data include erroneously labeled basecalling data, an optional method 700 can be performed to clean the training data.

FIG. 7 is a flowchart illustrating a method 700 for cleaning a training dataset in accordance with an embodiment of the present invention. As described above, an original (or uncleaned) training dataset may be provided to train the one or more neural network models in base network (e.g., base network 450). The base network generates confidence level scores and basecalling predictions. One or more filtering methods (e.g., methods 500 and 600 described above) can be used to filter the sequences in the uncleaned training dataset. The sequences that pass the filter are used as a new training dataset (or a retraining dataset) to replace the previous training dataset.

In particular, as shown in FIG. 7, the training dataset cleaning method 700 may begin with step 702, which obtains a retraining dataset including only sequences that previously passed filtering (e.g., in methods 500 or 600). Step 704 retrains one or more neural network models (e.g., models 452 in base network 450) using the retraining dataset. In step 706, based on the retraining dataset (which has been filtered to include only high-quality sequences), the one or more neural network models in the base network redetermines confidence level scores and basecalling predictions. In some embodiments, the one or more neural network models in the base network does not generate the SQFN indices in the retraining process. In step 708, the retraining dataset is filtered using the redetermined confidence level scores. The filtering process of the retraining dataset can be the same or similar to methods 500 and 600 described above, and is thus not repeatedly described. Step 710 determines if all sequences in the retraining dataset pass the filter. For example, if the filtering process (e.g., methods 500 or 600) determines that not all the sequences in the retraining dataset are high-quality sequences, step 710 determines that not all sequences pass the filter. The method 700 can then repeat steps 702, 704, 706, 708, and 710. As described above, during the filtering the process, a threshold number is used for comparing to the number of correctly-classified bases in a sequence. The threshold number can be fixed or adaptive. For instance, the threshold number can be configured such that it progressively increases over the repetitions of the filtering and cleaning processes. Eventually, if step 710 determines that all sequences in a retraining dataset pass the filter, which indicates that all sequences are considered high-quality sequences, the method 700 may proceed to an end. The high-quality sequences are used as the new training data. The new training data thus represent a cleaned training dataset that only include high-quality sequences. Using the new training data, the training of the neural network models can be improved. In turn, the trained neural network models can make more accurate basecalling predictions.

In general, a base network trained by using only a high-quality training dataset (e.g., a cleaned training dataset) can provide higher prediction accuracy than a network trained by dataset having the original training dataset (e.g., an uncleaned training dataset). In some embodiments, for a base network trained by using only a cleaned training dataset, its confidence level scores may not establish a strong bias toward the data quality. Therefore, in some cases, the basecalling predictions are generated by a based network trained with a cleaned dataset, while the confidence level scores used for the BCQF process are generated by a base network trained using an uncleaned training dataset. In some embodiments, multiple neural network models are used in a base network so that, for example, one model can be trained by using a cleaned training dataset and another model can be trained by using an uncleaned training dataset. As a result, the processing speed and efficiency can be improved. In some embodiments, two independent base networks can be partially integrated to share a same backbone network but have different decoders for providing different outputs (e.g., one for providing basecalling prediction and one for providing confidence level scores). The various network structures are described in more detail below.

Figures 8A, 8B:
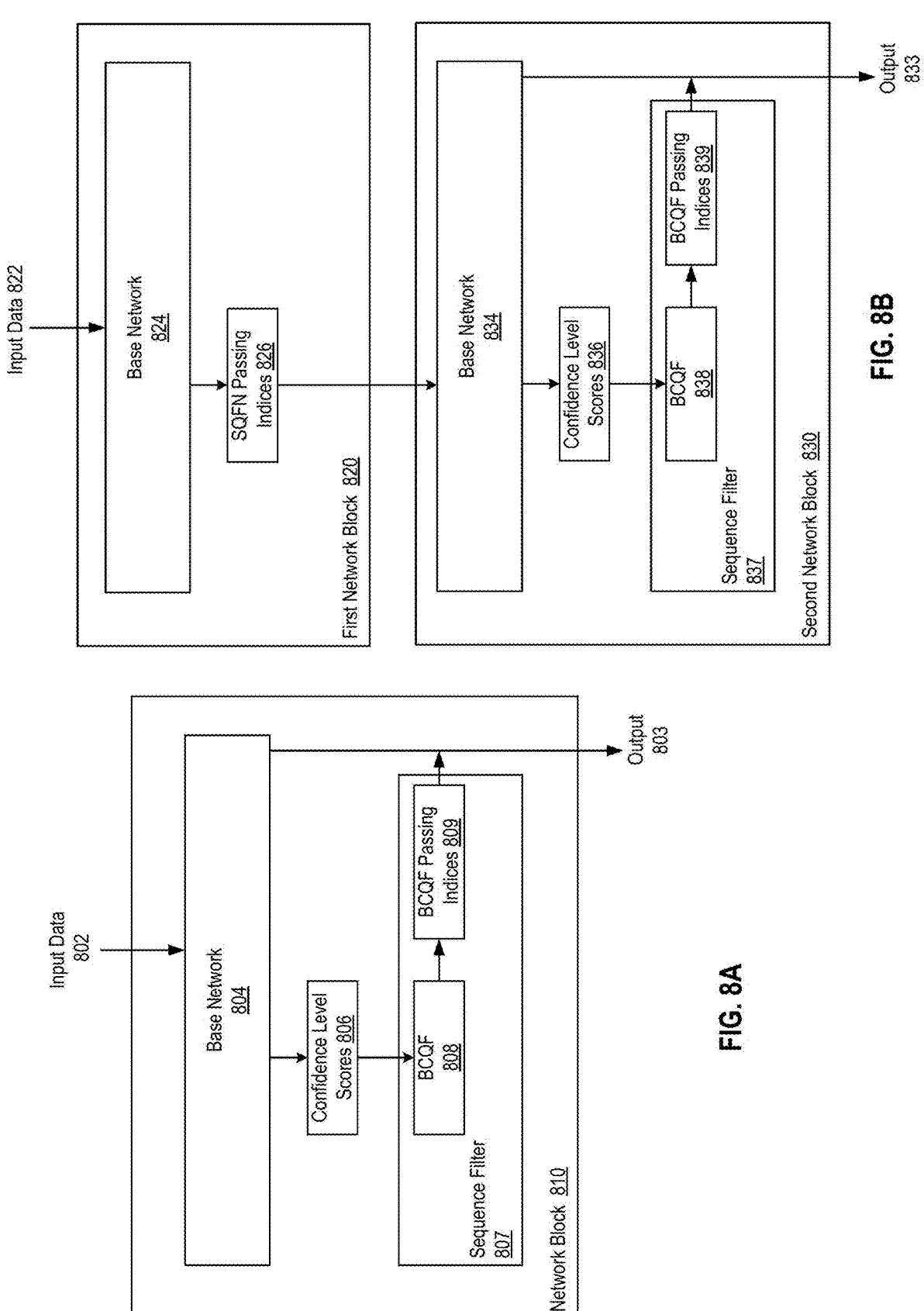
FIG. 8A is a block diagram illustrating a hierarchical processing network structure for basecalling using one network block in accordance with an embodiment of the present invention.
FIG. 8B is a block diagram illustrating a hierarchical processing network structure for basecalling using two network blocks in accordance with another embodiment of the present invention.

FIG. 8A is a block diagram illustrating an embodiment of hierarchical processing network structure 400 for basecalling using one network block. As shown in FIG. 8A, the network structure 400 in this embodiment includes a network block 810. Network block 810 receives input data 802, which include nucleic acid sequences. The sequences may be unknown sequences, from which basecalling is to be performed for base predictions. The sequences may have high-quality sequences and/or low quality sequences. Network block 810 includes a based network 804 and a sequence filter 807, which are the same as or similar to base network 450 and sequence filter 460, respectively, as shown in FIG. 4. In some embodiments, base network 804 generates confidence level scores 806 and provide the scores 806 to sequence filter 807. Sequence filter 807 performs the basecalling quality filtering (BCQF) process based on confidence level scores 806. The BCQF process is described above. Sequence filter 807 generates, based on the BCQF results, passing indices 809 representing the quality of the one or more sequences in the input data 802. Sequence filter 807 can thus filter the sequences in the input data 802 based on the BCQF passing indices 809. The filtering can be performed using methods described above (e.g., method 500). After filtering, high-quality sequences are obtained and base network 804 can make basecalling predictions using the high-quality sequences. The basecalling predictions and/or the BCQF passing indices 809 can be provided as output 803 of network block 810.

FIG. 8B is a block diagram illustrating another embodiment of a hierarchical processing network structure for basecalling using two network blocks 820 and 830. With reference to FIG. 8B, first network block 820 receives input data 822 comprising a group of nucleic acid sequences. The sequences may be unknown sequences, from which basecalling is to be performed for base predictions. The sequences may have high-quality sequences and/or low quality sequences. First network block 820 includes a base network 824 but no sequence filter. Second network block 830 includes a base network 834 and a sequence filter 837. In some embodiments, base network 824 determines first passing indices (e.g., SQFN passing indices 826) using the one or more neural network models of base network 824. The first passing indices are provided to base network 834 of second network block 830. As described above, a SQFN passing index indicates whether a particular sequence is a high-quality sequence. Based on the SQFN passing indices, base network 834 can process only the high-quality sequences provided by first network block 820.

As shown in FIG. 8B, base network 834 of the second network block 830 determines confidence level scores associated with sequences received by the second network block 830. The sequence filter 837 of second network block 830 performs the BCQF process 838 and generates second passing indices (e.g., BCQF passing indices 839). Thus, the sequence filter 837 can filter the sequences received by the second network block to obtain high-quality sequences. The filtering can be performed using the BCQF process described above. Base network 834 can perform basecalling predictions using the high-quality sequences obtained as the filtered results. The basecalling predictions, the high-quality sequences, and/or the BCQF passing indices 839 can be provided as an output 833 of second network block 830.

Figures 8C, 8D:
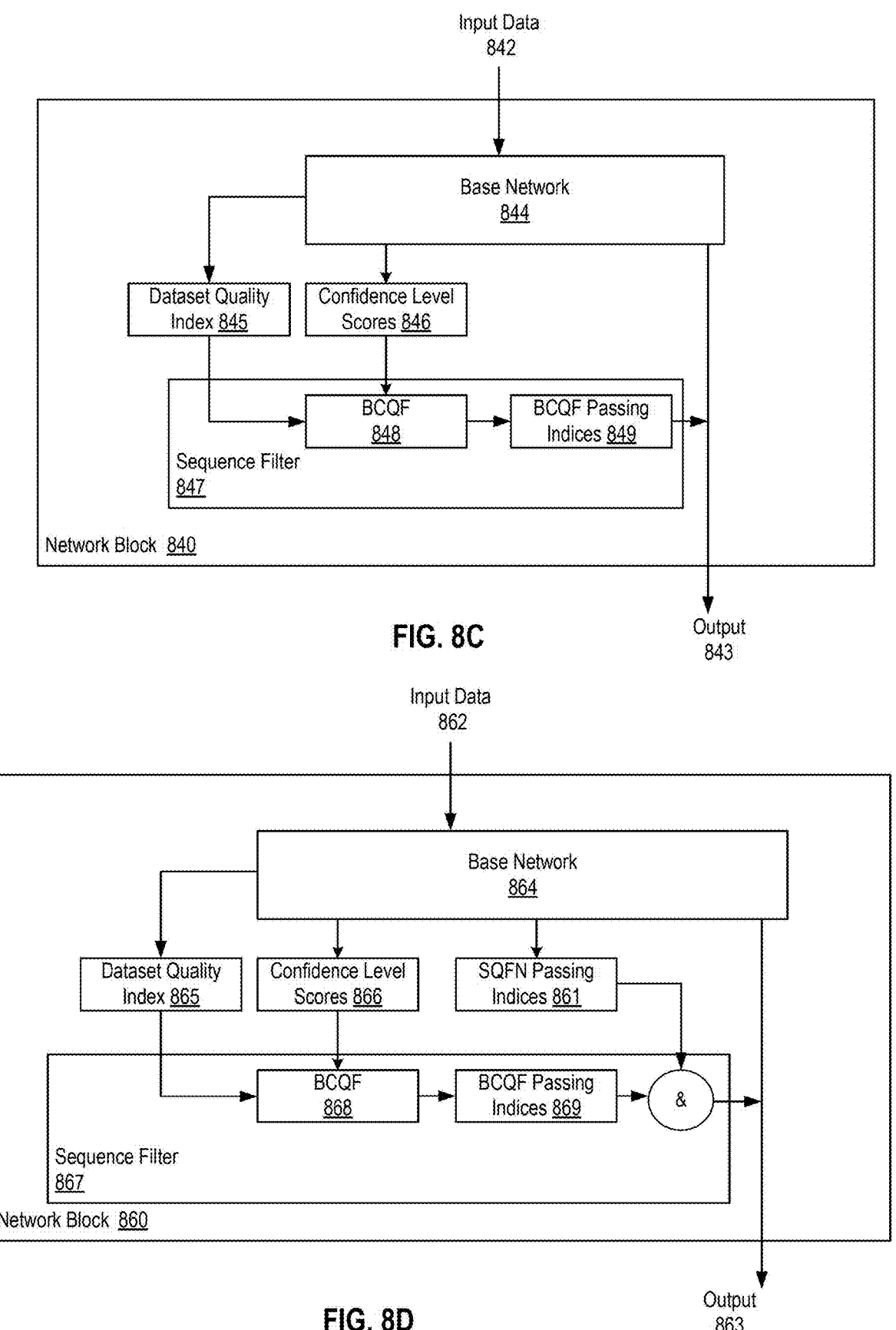
FIG. 8C is a block diagram illustrating a hierarchical processing network structure for basecalling using one network block in accordance with another embodiment of the present invention.
FIG. 8D is a block diagram illustrating a hierarchical processing network structure for basecalling using one network block in accordance with another embodiment of the present invention.

FIG. 8C is a block diagram illustrating another embodiment of hierarchical processing network structure 400 for basecalling using one network block 840. With reference to FIG. 8C, network block 840 receives input data 842 comprising a group of nucleic acid sequences. The sequences may be unknown sequences, from which basecalling is to be performed for base predictions. The sequences may have high-quality sequences and/or low quality sequences. Network block 840 includes a base network 844 and a sequence filter 847, which can be the same or similar to base network 450 and sequence filter 460, respectively, as show in FIG. 4. In some embodiments, base network 844 includes one or more neural network based models that can generate confidence level scores 846 and dataset quality index 845. Based network 844 provides the scores 846 to sequence filter 847. Base network 844 can also provide the dataset quality index 845 to sequence filter 847, so that sequence filter 847 can perform an adaptive BCQF process. In an adaptive BCQF process, the threshold number of high-quality bases for classifying whether a sequence is a high-quality sequence varies based on the dataset quality index 845. For example, if the dataset quality index has a high numerical value, the threshold number may be decreased, and vice versa. Sequence filter 847 can perform a BCQF process based on confidence level scores 846 and the adaptive threshold number. The BCQF method is described above. Sequence filter 847 generates, based on the BCQF results, BCQF passing indices 849 representing the quality of the one or more sequences in the input data 842. Sequence filter 847 can thus filter the sequences in the input data 842 based on the BCQF passing indices 849. The filtering can be performed using methods described above (e.g., method 500). After filtering, high-quality sequences are obtained and base network 844 can make basecalling predictions using the high-quality sequences. The basecalling predictions and/or the BCQF passing indices 849 can be provided as output 843 of network block 840.

FIG. 8D is a block diagram illustrating another embodiment of hierarchical processing network structure 400 for basecalling using one network block 860. With reference to FIG. 8D, network block 860 receives input data 862 comprising a group of nucleic acid sequences. The sequences may be unknown sequences, from which basecalling is to be performed for base predictions. The sequences may have high-quality sequences and/or low quality sequences. Network block 860 includes a base network 864 and a sequence filter 867, which can be the same or similar to base network 450 and sequence filter 460, respectively, as show in FIG. 4. In some embodiments, base network 864 includes one or more neural network based models that can generate confidence level scores 866, dataset quality index 865, and SQFN passing indices 861. Based network 864 provides the scores 866 and dataset quality index 865 to sequence filter 867. Sequence filter 847 can perform an adaptive BCQF process similar to those described above. For example, sequence filter 867 can perform an adaptive BCQF process based on confidence level scores 866 and an adaptive threshold number set by using the dataset quality index 865. Sequence filter 867 generates, based on the BCQF results, BCQF passing indices 869 representing the quality of the one or more sequences in the input data 862.

In the embodiment shown in FIG. 8D, SQFN passing indices 861 are also generated. SQFN passing indices 861 represent the quality of the one or more sequences in input data 862 as determined by base network 864. The sequence filter 867 can perform a logic operation (e.g., an AND) by using both the SQFN passing indices 861 and BCQF passing indices 869. For example, in the below table, "true" and "false" or "1" and "0" represent "pass" or "fail", respectively, in both a SQFN passing index 861 and a BCQF passing index 869. If the logic operation is an AND operation, the combined passing index resulting from the logic operation is a "pass" only if both the SQFN passing index 861 and the BCQF passing index 869 are "true" or "1".

| SQFN passing index | BCQF passing index | Combined passing index |
|---|---|---|
| A | B | Y = A · B |
| 0 (false or fail) | 0 (false or fail) | 0 (false or fail) |
| 0 (false or fail) | 1 (true or pass) | 0 (false or fail) |
| 1 (true or pass) | 0 (false or fail) | 0 (false or fail) |
| 1 (true or pass) | 1 (true or pass) | 1 (true or pass) |

With reference still to FIG. 8D, sequence filter 867 can thus filter the sequences in the input data 862 based on the combined passing indices. The filtering can be performed by using methods described above (e.g., method 500). After filtering, high-quality sequences are retained and base network 864 can make basecalling predictions using just the high-quality sequences. The basecalling predictions and/or the combined passing indices can be provided as output 863 of network block 860.

Figure 8E:
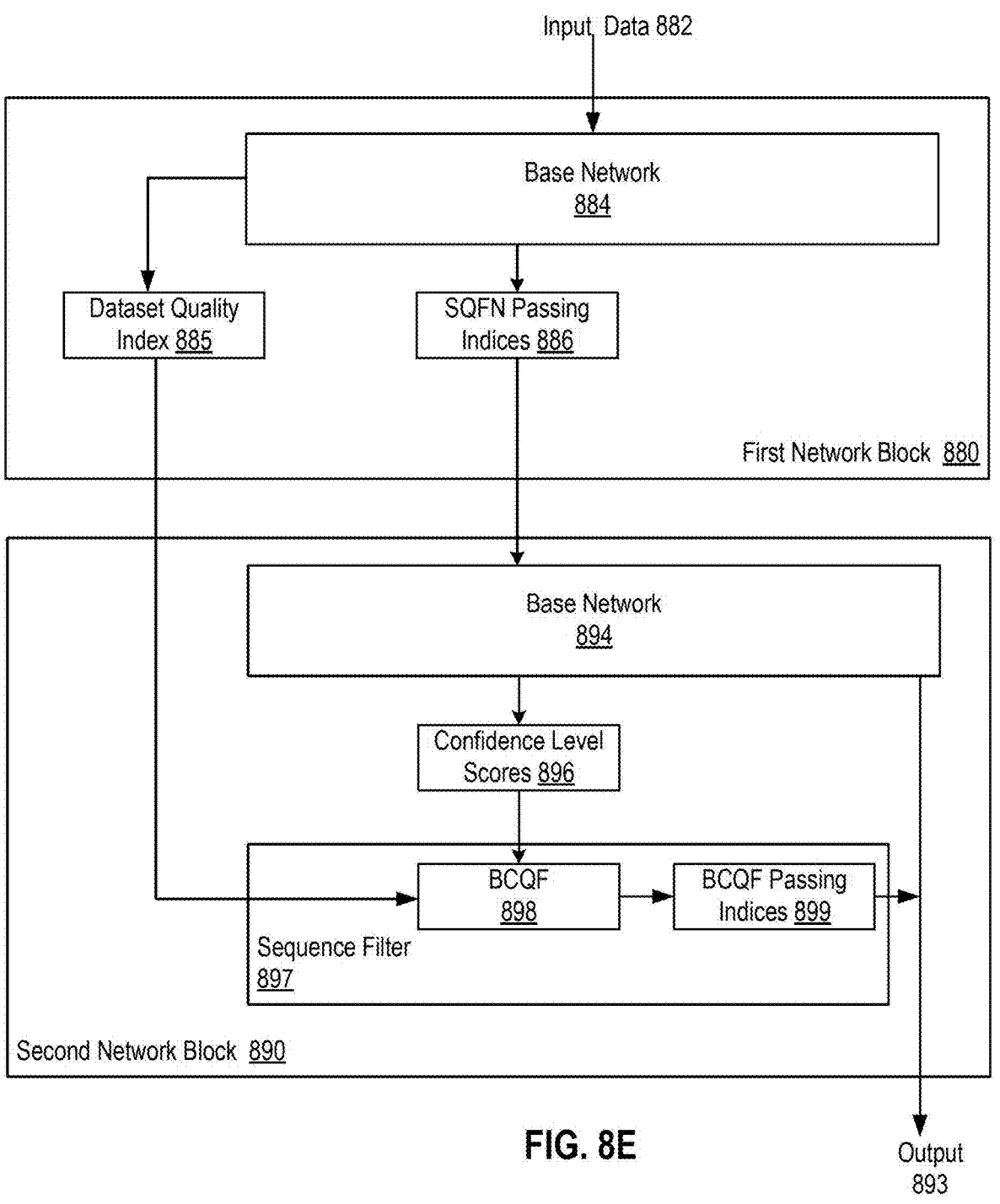
FIG. 8E is a block diagram illustrating a hierarchical processing network structure for basecalling using two network blocks in accordance with another embodiment of the present invention.

FIG. 8E is a block diagram illustrating another embodiment of a hierarchical processing network structure 400 for basecalling using two network blocks 880 and 890. With reference to FIG. 8E, first network block 880 receives input data 882 comprising a group of nucleic acid sequences. The sequences may be unknown sequences, from which basecalling is to be performed for base predictions. The sequences may have high-quality sequences and/or low quality sequences. First network block 880 includes a base network 884 but no sequence filter. Second network block 890 includes a base network 894 and a sequence filter 897. In some embodiments, base network 884 determines first passing indices (e.g., SQFN passing indices 886) using the one or more neural network based models of base network 884. The first passing indices (e.g., SQFN passing indices 886) are provided to base network 894 of second network block 890. As described above, a SQFN passing index indicates whether a particular sequence is a high-quality sequence. Based on the SQFN passing indices 886, base network 894 processes the high-quality sequences provided by first network block 880.

As shown in FIG. 8E, in some embodiments, base network 884 in first network block 880 also generates and provides dataset quality index 885 to the sequence filter 897 of the second network block 890, such that an adaptive BCQF process can be performed. Base network 894 of the second network block 890 determines confidence level scores associated with sequences received by the second network block 890. The sequence filter 897 of second network block 890 performs the BCQF process 898 and generates second passing indices (e.g., BCQF passing indices 899). Thus, the sequence filter 897 can filter the sequences received by the second network block to obtain high-quality sequences. The filtering can be performed using the BCQF process described above. The BCQF process can be an adaptive process by setting the threshold number of bases for classifying a high-quality sequence using the dataset quality index 885. Base network 894 can perform basecalling predictions using the high-quality sequences obtained as the filtered results. The basecalling predictions, the high-quality sequences, and/or the BCQF passing indices 899 can be provided as an output 893 of second network block 890.

FIGS. 8A-8E illustrate various examples of network structure 400, including using one or two network blocks and various combinations of sequencing quality indicators (e.g., one or more of the dataset quality index, the SQFN passing indices, the confidence level scores). It is understood that other variations, combinations of the blocks, or embodiments of network structure 400 can also be implemented without departing from the illustrated principle. For example, three or more network blocks may be used, and the basecalling predictions may be performed by the first network block or the last network block.

Figure 9A:
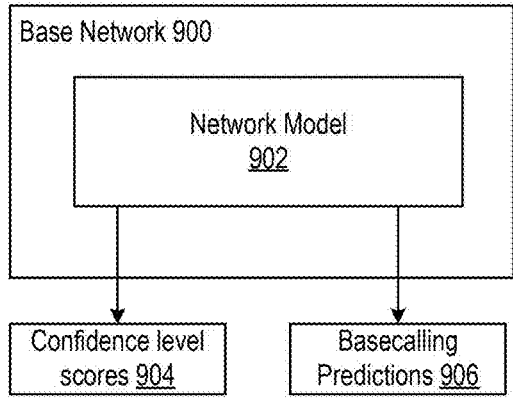
FIGS. 9A-9G are block diagrams illustrating base networks in accordance with different embodiments of the present invention.
Figure 9B:
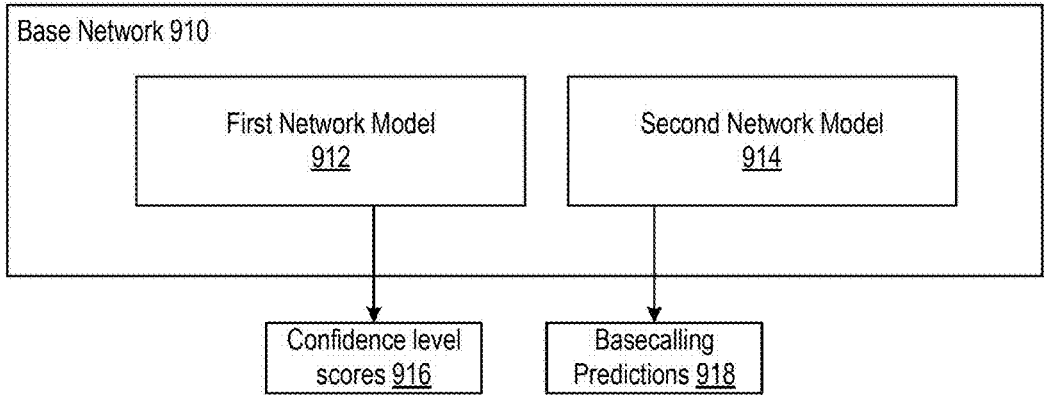

FIGS. 9A-9G are a block diagram illustrating various embodiments of a base network in accordance with different embodiments of the present invention. FIG. 9A illustrates that a base network 900 includes a single network model 902 that is used to generate both confidence level scores 904 and basecalling predictions 906. FIG. 9B illustrates that a base network 910 includes two network models 912 and 914. First network model 912 is used to generate the confidence level scores 916 and second network model 914 is used to make the basecalling predictions 918. As described above, the two network models 912 and 916 can be trained differently using different training dataset (e.g., an uncleaned training data and a cleaned training dataset), thereby providing both accurate basecalling predictions and improved confidence level scores.

Figure 9C:
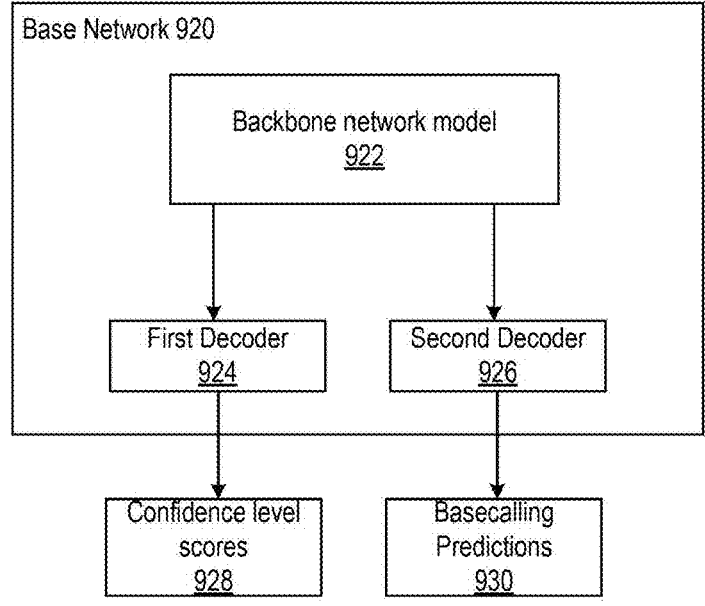

FIG. 9C illustrates another embodiment of a base network 920 that includes a backbone network model 922 and two decoders 924 and 926. Instead of using two separate network models as shown in FIG. 9B, a backbone network can be shared between the two network models, thereby partially combining the two network models, that can increase the inference speed of the networks. The backbone network model 922 can use, for example, a 1-dimensional CNN-base model, a transformer-based model, an RNN-base model, and/or any other desired neural network structures. Some examples of the backbone network model are described in more detail below. In base network 920 shown in FIG. 9C, first decoder 924 is used to generate confidence level scores 928 and second decoder 926 is used to make basecalling predictions 930. The two decoders 924 and 926 are used to generate different outputs and therefore improves the computational efficiency. Similar to those described above, the two decoders 924 and 926 can be trained differently using different training dataset (e.g., an uncleaned training data and a cleaned training dataset), thereby providing both accurate basecalling predictions and improved confidence level scores.

Figure 9D:
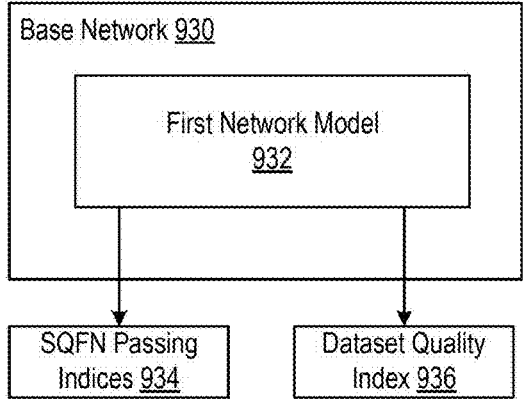
Figure 9E:
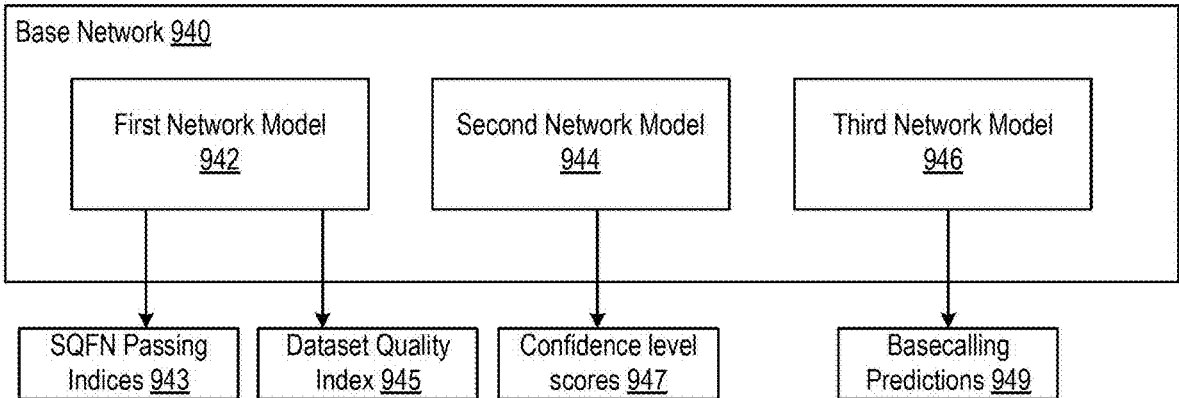

FIG. 9D illustrates that a base network 930 includes a single network model 932 that is used to generate both SQFN passing indices 934 and dataset quality index 936. FIG. 9E illustrates that a base network 940 includes three network models 942, 944, and 946. First network model 942 is used to generate the SQFN passing indices 943 and dataset quality index 945. Second network model 944 is used to generate the confidence level scores 947. Third network model 946 is used to make the basecalling predictions 949. Similar to those described above, the three network models 942, 944, and 946 can be trained differently using different training dataset (e.g., uncleaned training datasets and cleaned training datasets), thereby providing both accurate basecalling predictions and improved confidence level scores. By using multiple network models in a base network, the performance of the network block can be improved.

Figure 9F:
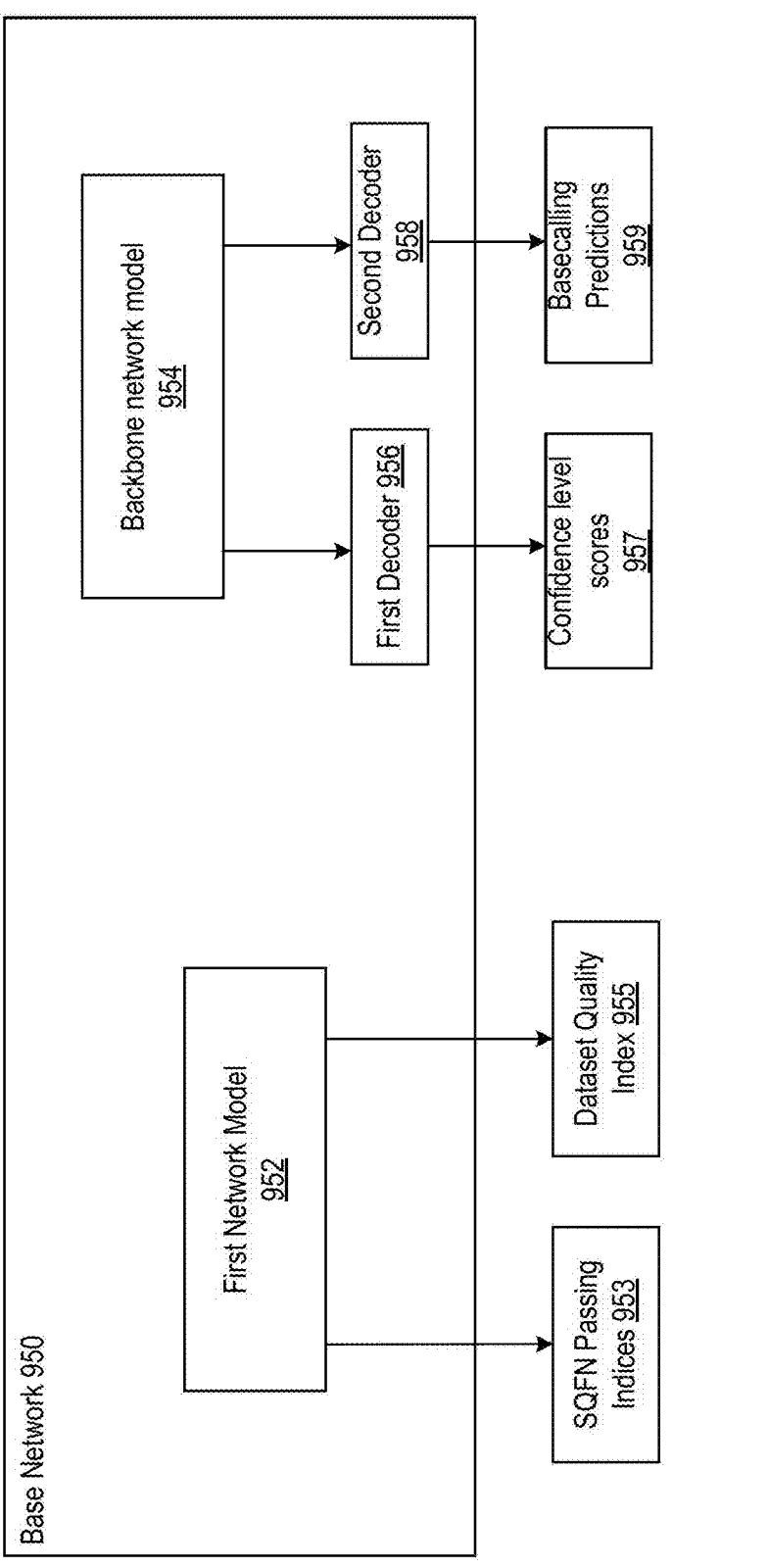

FIG. 9F illustrates an example that a base network 950 includes a first network model 952 that is used to generate both SQFN passing indices 953 and dataset quality index 955. Base network 950 also includes a backbone network model 954 and two decoders 956 and 958. The first decoder 956 is used to generate the confidence level scores 957. The second decoder 958 is used to make the basecalling predictions 959. Similar to those described above, the first network model 952, the first decoder 956, and the second decoder 958 can be trained differently using different training dataset (e.g., uncleaned training datasets and cleaned training datasets), thereby providing both accurate basecalling predictions and improved confidence level scores. By using multiple network models in a base network, the performance of the network block can be improved.

Figure 9G:
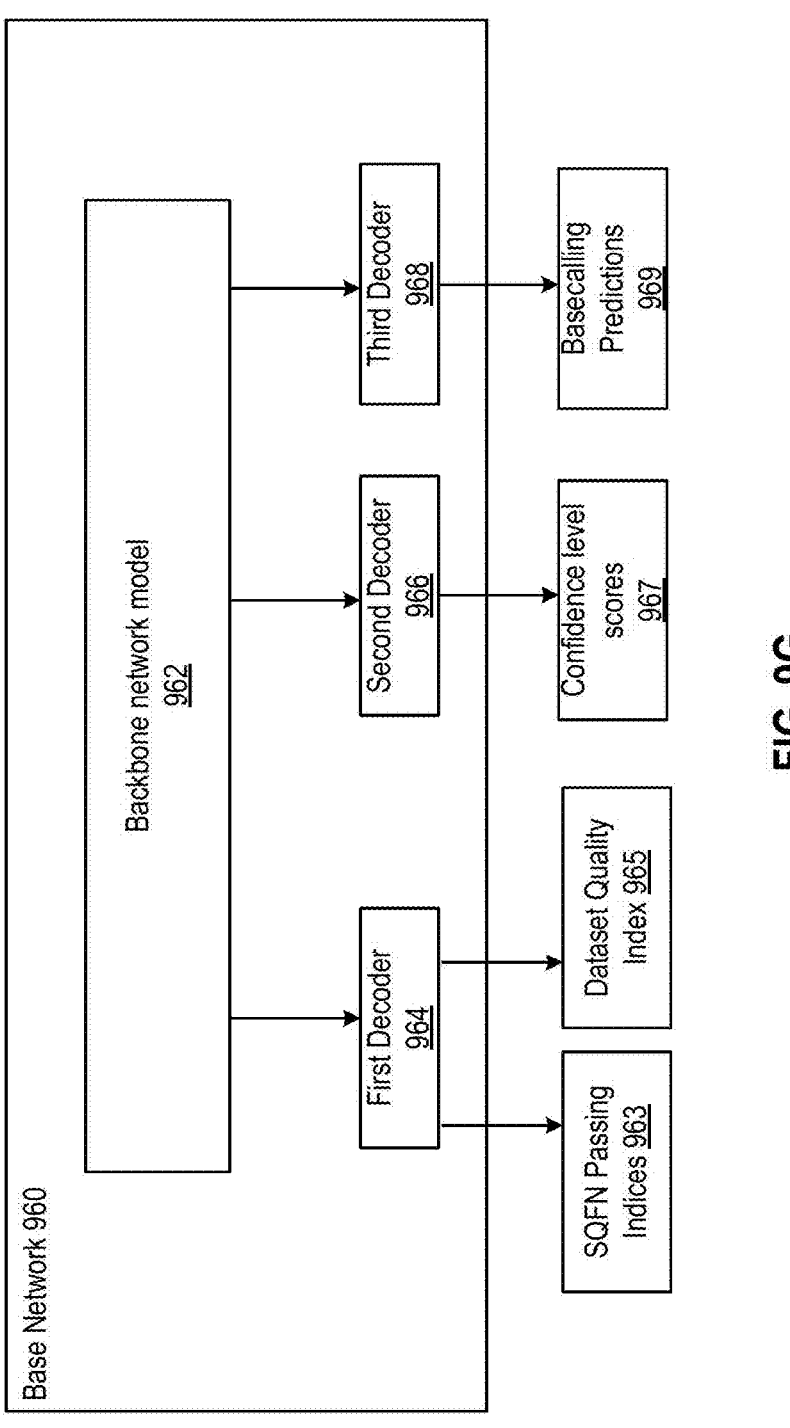

FIG. 9G illustrates that a base network 960 includes a backbone network model 962 that is shared between three decoders 964, 966, and 968. The backbone network model 922 can use, for example, a 1-dimensional CNN-base model, a transformer-based model, an RNN-base model, and/or any other desired neural network structures. Some examples of the backbone network model are described in more detail below. The first decoder 964 is used to generate SQFN passing indices 963 and dataset quality index 965. The second decoder 966 is used to generate the confidence level scores 967. The third decoder 968 is used to make the basecalling predictions 969. Similar to those described above, one or more of the three decoders 964, 966, and 968 can be trained differently using different training dataset (e.g., uncleaned training datasets and cleaned training datasets), thereby providing both accurate basecalling predictions and improved confidence level scores. By using multiple decoders sharing a backbone network model in a base network, the processing speed and efficiency can be improved.

Figure 10A:
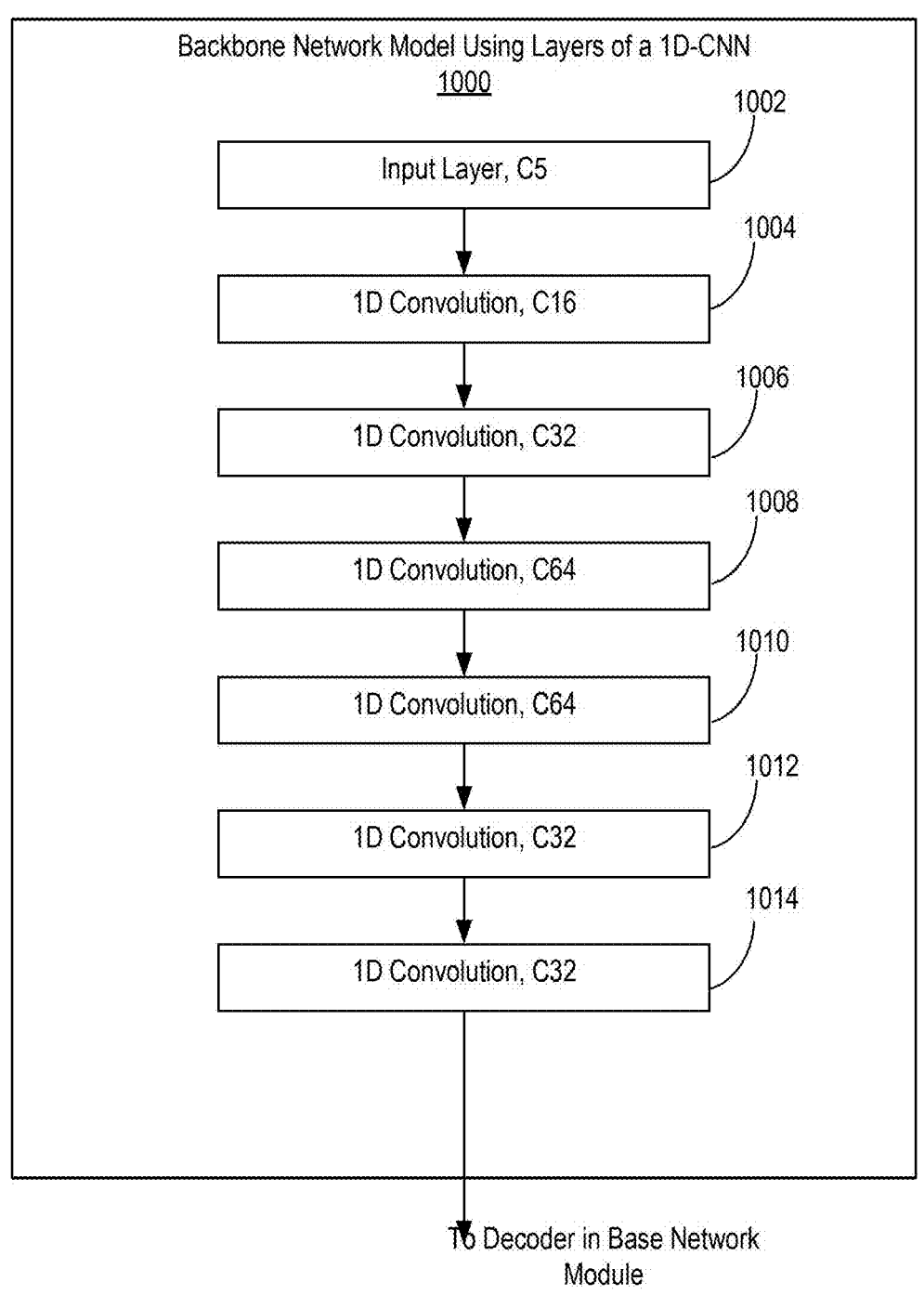
FIG. 10A is a block diagram illustrating a backbone network model using layers of a 1-dimensional (1D) CNN in accordance with one embodiment of the present invention.

As described above, some base network embodiments use a backbone network model and one or more decoders. A backbone network model can be a deep learning network model without the last several layers (e.g., the layers for making the final classification predictions and generating confidence levels). These layers may include pooling layer, a linear layer, a Softmax layer, etc. A decoder can have the equivalent functions as these last several layers. FIG. 10A is a block diagram illustrating a backbone network model 1000 using layers of a 1-dimensional CNN in accordance with one embodiment of the present invention. Model 1000 uses multiple layers including an input layer 1002 and multiple 1D convolution layers 1004-1014 as shown in FIG. 10A. The input layer 1002 receives the input data comprising multiple sequences. These sequences can be unknown nucleic acid sequences and include a mix of high-quality and low-quality sequences. These sequences may be represented by vectors. The sequences may represent clusters of fluorescence signals from multiple cycles. Input layer 1002 may be a linear layer. A linear layer is a type of feed-forward layer capable of learning an offset and a rate of correlation between the input and output of the linear layer. The linear layer can learn scaling automatically such that it can reduce or expand dimensions of the input vectors. In one embodiment shown in FIG. 10A, input layer 1002 can has 5 channels, the 1D convolution layer 1004 has 16 channels; the 1D convolution layer 1006 has 32 channels, and so forth as shown in FIG. 10A. A 1-dimensional convolution layer performs convolution operations in one direction, rather than two directions in a 2-dimensional convolution layer. For example, the input to 1-dimensional convolution layer

1004 is a 1-dimensional vectors (e.g., 1D feature vector representing signals at the center of the cluster of fluorescence signals).

In some embodiments, each of the 1-dimensional convolution layers 1004-1014 has a kernel for performing convolution operation. The kernel may have, for example, a size of 4 and a stride of 1. The stride is the number of pixels shifts over the input matrix. Therefore, if the stride is 1, the kernel (or filter) is moved 1 pixel at a time. In some embodiments, to keep the size of features constant, the padding may be configured to be 3, one at the head and two at the tail. A padding refers to the number of pixels added to an image when it is being processed by the kernel of the 1-dimensional convolution layer. As shown in FIG. 10A, backbone network model 1000 does not include the several last layers or a decoder. The output of backbone network model 1000 can be provided to multiple decoders or other layers for generating different desired outputs.

Figure 10B:
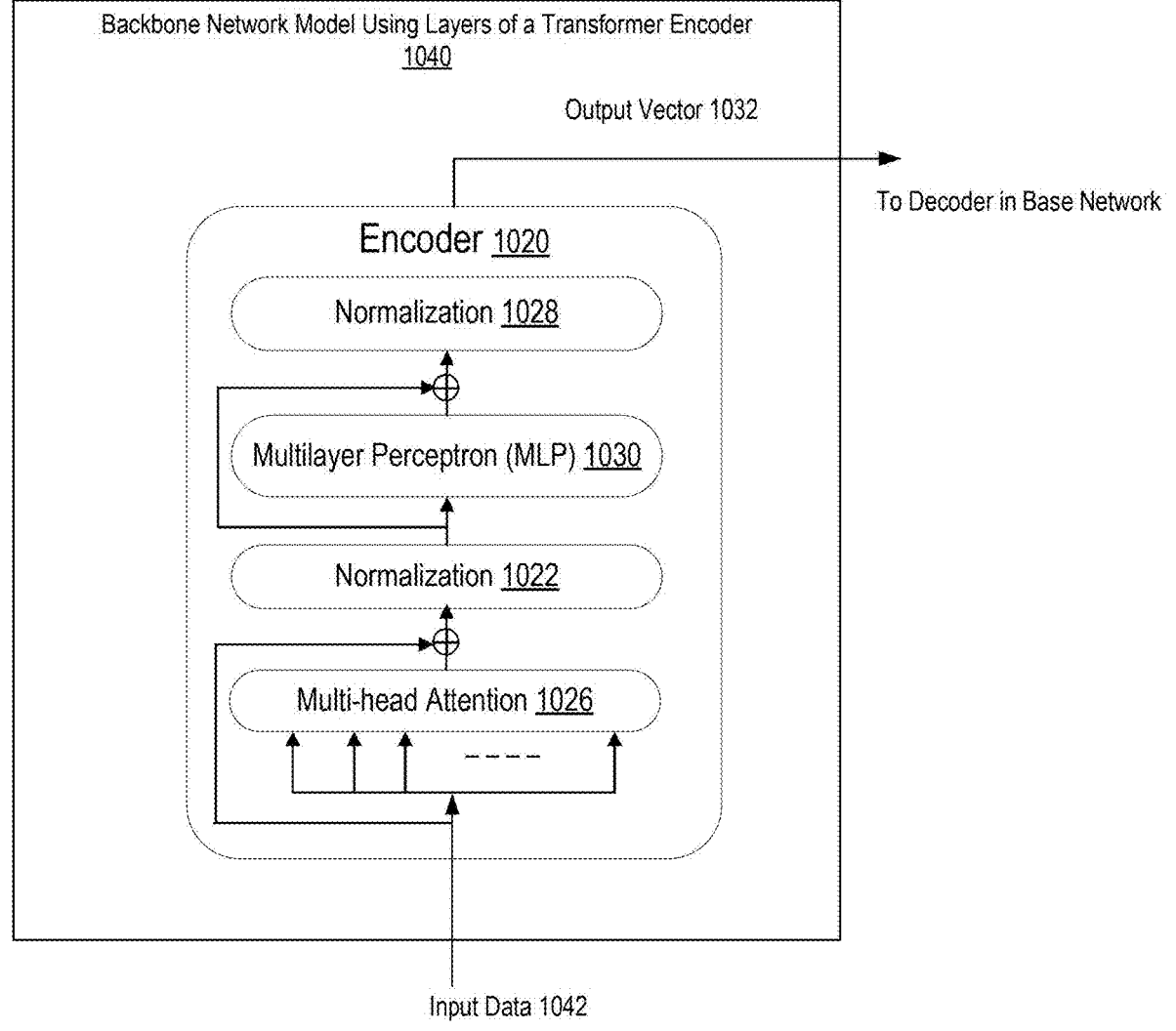
FIG. 10B is a block diagram illustrating a backbone network model using layers of a transformer encoder in accordance with one embodiment of the present invention.

FIG. 10B is a block diagram illustrating a backbone network model 1040 using layers of an encoder of a transformer based neural network, in accordance with one embodiment of the present invention. A transformer neural network has an encoder-decoder architecture using one or more attention layers. A transformer neural network can process multiple input sequences or vectors in parallel. Therefore, both the processing efficiency and speed of training of the network are greatly improved. Further, a transformer neural network uses one or more multi-headed attention layers for better interpreting or emphasizing on the important aspects of the input embedding vectors. The vanishing gradient issue is also eliminated or significantly reduced by the transformer neural network. In FIG. 10B, the backbone network model 1040 receives input data 1042, which can be sequences or vectors. In some embodiments, the input data 1042 may be provided to a position encoding layer (not shown) to account for the order of the feature vector elements. The position encoding layer includes a positional encoder, which is a vector that provides context according to the position of the elements in the vector. The position encoding layer generates position encoded vectors, which are provided to encoder 1020.

Encoder 1020 can be a self-attention based encoder. Encoder 1020 includes a multi-head attention layer 1026. The multi-head attention layer 1026 determines multiple attention vectors per element of the position encoded vectors and takes a weighted average to compute a final attention vector for each element of the position encoded vectors. The final attention vectors capture the contextual relationship between elements of the position encoded vectors. In some embodiments, encoder 1020 also includes one or more normalization layers 1022 and 1028. The normalization layers control the gradient scales. In some embodiments, the normalization layer 1022 is positioned after the multi-head attention layer 1026, as illustrated in FIG. 10B. In some embodiments, the normalization layer can be positioned before the multi-head attention layer. Similarly, it can be positioned before or after multiplayer perceptron layer (MLP) 1030 as well. A normalization layer standardizes the inputs to the next layer, which has the effect of stabilizing the network's learning process and reducing the number of training iterations required to train the deep learning network. Normalization layer 1022 and 1028 can perform batch normalization and/or layer normalization.

FIG. 10B also illustrates that encoder 1020 includes a multilayer perceptron (MLP) 1030. MLP 1030 is a type of feedforward neural network. An MLP has layers of nodes including: an input layer, one or more hidden layers, and an output layer. Except for the input nodes, each node in an MLP is a neuron that uses nonlinear activation function. MLP 1030 is applied to every normalized attention vector. MLP 1030 can transform the normalized attention vectors to a form that is acceptable by the next encoder or decoder in network model 1040. In the example shown in FIG. 10B, one encoder is used. Thus, in FIG. 10B, the output of MLP 1030, after normalized by normalization layer 1028, is the encoder output vectors 1032. Encoder output vectors 1032 are then provided to a decoder in a base network (e.g., base network 920, 950, or 960). In other embodiments, a stacked encoder structure having two encoders can be used. Thus, the output vectors from encoder 1020 may also be provided to the next encoder as input vectors.

In a backbone network model using layers of a transformer network model, all the attention vectors (or those after normalization) are independent from one another. Therefore, they can be provided to the MLP 1030 in parallel. Encoder 1020 can thus generate encoder output vectors 1032 for all the input embedding vectors in the input data 1042 in parallel, thereby significantly improving the processing speed. Some embodiments of the 1D CNN network model and the transformer network model are described in more detail in International Application No. PCT/CN2021/141269.

Exemplary Computing Device Embodiment

Figure 11:
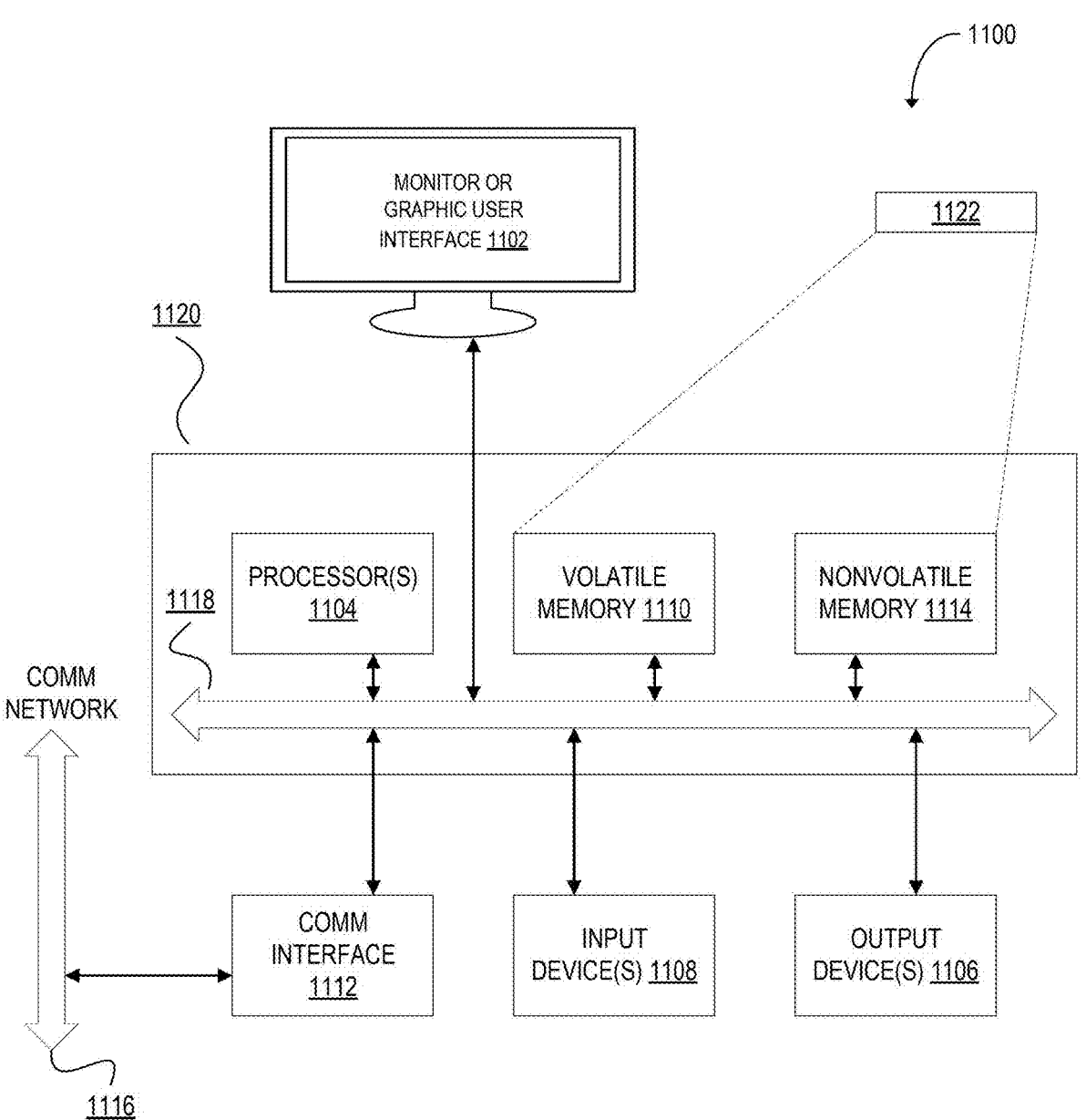
FIG. 11 illustrates a block diagram of an exemplary computing device that may incorporate embodiments of the present invention.

FIG. 11 is an example block diagram of a computing device 1100 that may incorporate embodiments of the present invention. FIG. 11 is merely illustrative of a machine system to carry out aspects of the technical processes described herein, and does not limit the scope of the claims. One of ordinary skill in the art would recognize other variations, modifications, and alternatives. In one embodiment, the computing device 1100 typically includes a monitor or graphical user interface 1102, a data processing system 1120, a communication network interface 1112, input device(s) 1108, output device(s) 1106, and the like.

As depicted in FIG. 11, the data processing system 1120 may include one or more processor(s) 1104 that communicate with a number of peripheral devices via a bus subsystem 1118. These peripheral devices may include input device(s) 1108, output device(s) 1106, communication network interface 1112, and a storage subsystem, such as a volatile memory 1110 and a nonvolatile memory 1117. The volatile memory 1110 and/or the nonvolatile memory 1117 may store computer-executable instructions and thus forming logic 1122 that when applied to and executed by the processor(s) 1104 implement embodiments of the processes disclosed herein.

The input device(s) 1108 include devices and mechanisms for inputting information to the data processing system 1120. These may include a keyboard, a keypad, a touch screen incorporated into the monitor or graphical user interface 1102, audio input devices such as voice recognition systems, microphones, and other types of input devices. In various embodiments, the input device(s) 1108 may be embodied as a computer mouse, a trackball, a track pad, a joystick, wireless remote, drawing tablet, voice command system, eye tracking system, and the like. The input device(s) 1108 typically allow a user to select objects, icons, control areas, text and the like that appear on the monitor or graphical user interface 1102 via a command such as a click of a button or the like. Graphical user interface 1102 can be used in step 1618 of method 1600 to receive user inputs for making the corrections of bases or sequences in a data labelling process.

The output device(s) 1106 include devices and mechanisms for outputting information from the data processing system 1120. These may include the monitor or graphical user interface 1102, speakers, printers, infrared LEDs, and so on as well understood in the art.

The communication network interface 1112 provides an interface to communication networks (e.g., communication network 1116) and devices external to the data processing system 1120. The communication network interface 1112 may serve as an interface for receiving data from and transmitting data to other systems. Embodiments of the communication network interface 1112 may include an Ethernet interface, a modem (telephone, satellite, cable, ISDN), (asynchronous) digital subscriber line (DSL), Fire-Wire, USB, a wireless communication interface such as Bluetooth or WiFi, a near field communication wireless interface, a cellular interface, and the like. The communication network interface 1112 may be coupled to the communication network 1116 via an antenna, a cable, or the like. In some embodiments, the communication network interface 1112 may be physically integrated on a circuit board of the data processing system 1120, or in some cases may be implemented in software or firmware, such as "soft modems", or the like. The computing device 1100 may include logic that enables communications over a network using protocols such as HTTP, TCP/IP, RTP/RTSP, IPX, UDP and the like.

The volatile memory 1110 and the nonvolatile memory 1114 are examples of tangible media configured to store computer readable data and instructions forming logic to implement aspects of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 1110 and the nonvolatile memory 1114 may be configured to store the basic programming and data constructs that provide the functionality of the disclosed processes and other embodiments thereof that fall within the scope of the present invention. Logic 1122 that implements embodiments of the present invention may be formed by the volatile memory 1110 and/or the nonvolatile memory 1114 storing computer readable instructions. Said instructions may be read from the volatile memory 1110 and/or nonvolatile memory 1114 and executed by the processor(s) 1104. The volatile memory 1110 and the nonvolatile memory 1114 may also provide a repository for storing data used by the logic 1122. The volatile memory 1110 and the nonvolatile memory 1114 may include a number of memories including a main random access memory (RAM) for storage of instructions and data during program execution and a read only memory (ROM) in which read-only non-transitory instructions are stored. The volatile memory 1110 and the nonvolatile memory 1114 may include a file storage subsystem providing persistent (non-volatile) storage for program and data files. The volatile memory 1110 and the nonvolatile memory 1114 may include removable storage systems, such as removable flash memory.

The bus subsystem 1118 provides a mechanism for enabling the various components and subsystems of data processing system 1120 communicate with each other as intended. Although the communication network interface 1112 is depicted schematically as a single bus, some embodiments of the bus subsystem 1118 may utilize multiple distinct busses.

It will be readily apparent to one of ordinary skill in the art that the computing device 1100 may be a device such as a smartphone, a desktop computer, a laptop computer, a rack-mounted computer system, a computer server, or a tablet computer device. As commonly known in the art, the computing device 1100 may be implemented as a collection of multiple networked computing devices. Further, the computing device 1100 will typically include operating system logic (not illustrated) the types and nature of which are well known in the art.

One embodiment of the present invention includes systems, methods, and a non-transitory computer readable storage medium or media tangibly storing computer program logic capable of being executed by a computer processor. The computer program logic can be used to implement embodiments of processes and methods described herein, including method 300 for basecalling, method 400 for image preprocessing, method 800 for cluster detection, method 1000 for feature extraction, and various deep learning algorithms and processes.

Those skilled in the art will appreciate that computer system 1100 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the underlying principles of the invention as described by the various embodiments referenced above and below.

What is claimed is:

1. A computer-implemented method for enhanced training of one or more neural-network models to enhance the quality of basecalling results obtained by a high-throughput process for sequencing nucleic acid molecules using the one or more neural-network models, the method being performed by one or more computing devices, each comprising a processor and a memory, the method comprising:

obtaining, by the one or more computing devices, training data comprising fluorescence signal data corresponding to a plurality of nucleic acid sequences processed by a nucleic acid sequencing system;

processing, by the one or more computing devices, the training data using the one or more neural-network models thereby generating one or both of a confidence level and a basecalling prediction for each base in the plurality of nucleic acid sequences;

filtering, by the one or more computing devices, the training data to determine a filtered set of training data comprising fluorescence signal data corresponding to high-quality sequences in the plurality of nucleic acid sequences, wherein filtering comprises identifying the high-quality sequences using one or both of the confidence level and the basecalling prediction for each base in the plurality of sequences; and using, by the one or more computing devices, the filtered set of training data, to train one or more neural-network models to generate basecalling predictions;

wherein the one or more neural-network based models are included in one or more network blocks comprising a first network block and a second network block, and wherein generating one or both of a confidence level and a basecalling prediction comprises:

determining one or more first passing indices and a dataset quality index using one or more neural-network based models of the first network block, providing the first passing indices to one or more neural-network based models of the second network block, providing the dataset quality index to a sequence filter of the second network block; and determining, based on the one or more neural-network based models of the second network block, confidence level scores associated with bases included in sequences received by the second network block.

2. The method of claim 1, wherein identifying a high-quality sequence of the high-quality sequences comprises, with respect to a sequence of the plurality of nucleic acid sequences:

comparing the confidence level of each base in the sequence to a confidence level threshold to determine if each base is a high-quality base;

counting a number of high-quality bases in the sequence; and determining, based on the number of high-quality bases in the sequence, if the sequence is a high-quality sequence.

3. The method of claim 1, wherein the training data comprises labeled basecalling data, and wherein identifying a high-quality sequence of the high-quality sequences comprises, with respect to a sequence of the plurality of nucleic acid sequences:

determining, based on labeled basecalling data, if bases included in the sequence are correctly classified in the labeled basecalling data;

counting a number of correctly-classified bases in the sequence; and determining, based on the number of correctly-classified bases in the sequence, if the sequence is a high-quality sequence to determine if the sequence passes filtering.

4. The method of claim 3, further comprising:

obtaining a retraining dataset including only sequences that passed filtering;

retraining the one or more neural-network models using the retraining dataset to obtain one or more retained neural-network models, re-determining confidence level scores and basecalling predictions based on the one or more retrained neural-network models; and filtering the retraining data based on one or more re-determined confidence level scores and basecalling predictions.

5. The method of claim 1, wherein filtering the first group of sequences of nucleic acid comprises:

performing base calling quality filtering (BCQF) based on the dataset quality index and the confidence level scores associated with bases included in the sequences received by the second network block;

generating, based on BCQF results, second passing indices representing quality of the sequences received by the second network block; and filtering the sequences received by the second network block based on the second passing indices to obtain the second group of sequences of nucleic acid.

6. A system for enhanced training of one or more neural network models for enhancing quality of basecalling results obtained by a high-throughput process for sequencing nucleic acid molecules, the system comprises:

one or more processors of at least one computing device;

a communication interface; and a memory storing one or more instructions, when executed by the one or more processors, cause the one or more processors to perform steps comprising:

obtaining, by the one or more computing devices, training data comprising fluorescence signal data corresponding to a plurality of nucleic acid sequences processed by a nucleic acid sequencing system;

processing, by the one or more computing devices, the training data using the one or more neural networks thereby generating one or both of a confidence level and a basecalling prediction for each base in the plurality of nucleic acid sequences;

filtering, by the one or more computing devices, the training data to determine a filtered set of training data comprising fluorescence signal data corresponding to high-quality sequences in the plurality of nucleic acid sequences, wherein filtering comprises identifying the high-quality sequences using one or both of the confidence level and the basecalling prediction for each base in the plurality of sequences; and using, by the one or more computing devices, the filtered set of training data, to train one or more neural-network models to generate basecalling predictions;

wherein the one or more neural-network based models are included in one or more network blocks comprising a first network block and a second network block, and wherein generating one or both of a confidence level and a basecalling prediction comprises:

determining one or more first passing indices and a dataset quality index using one or more neural-network based models of the first network block, providing the first passing indices to one or more neural-network based models of the second network block, providing the dataset quality index to a sequence filter of the second network block; and determining, based on the one or more neural-network based models of the second network block, confidence level scores associated with bases included in sequences received by the second network block.

7. The system of claim 6, wherein the one or more of the plurality of sequencing quality indicators comprises at least one of:

sequence quality filtering network (SQFN) passing indices;

dataset quality indices; and confidence level scores.

8. The system of claim 7, wherein the one or more neural-network based models are a part of a single network block configured to determine the confidence level scores and the first group of sequences of nucleic acid.

9. The system of claim 7, wherein:

at least one of the one or more neural-network based models is included in a backbone network block,

the one or more neural-network based models include a first decoder and a second decoder, the first decoder and the second decoder being configured to receive outputs from the backbone network block, the first decoder is configured to determine one or more confidence level scores, and the second decoder is configured to determine the first group of sequences of nucleic acid.

10. The system of claim 6, wherein the one or more neural-network based models are a part of a single network block configured to determine one or more SQFN passing indices and one or more dataset quality indices.

11. The system of claim 7, wherein:

the first network block is being configured to determine SQFN passing indices and dataset quality indices;

the one or more neural-network based models include a first decoder and a second decoder, the first decoder and the second decoder being configured to receive outputs from a backbone network block, the first decoder is configured to determine one or more confidence level scores, and the second decoder is configured to determine the first group of sequences of nucleic acid.

12. The system of claim 7, wherein:

at least one of the one or more neural-network based models is included in a backbone network block, the one or more neural-network based models include a first decoder, a second decoder, and a third decoder, the first, second, and third decoders being configured to receive outputs from the backbone network block, the first decoder is configured to determine the SQFN passing indices and the dataset quality indices, the second decoder is configured to determine one or more confidence level scores, and the third decoder is configured to determine the first group of sequences of nucleic acid.

13. The system of claim 6, wherein:

the one or more neural-network based models are included in one or more network blocks comprising the first network block, the second network block, and a third network block;

the first network block is configured to determine SQFN passing indices and dataset quality indices;

the second network block is configured to determine confidence level scores; and the third network block is configured to determine the first group of sequences of nucleic acid.

14. A non-transitory computer readable medium comprising a memory storing one or more instructions which, when executed by one or more processors of at least one computing device, cause the at least one computing device to perform processing comprising:

obtaining, by the one or more computing devices, training data comprising fluorescence signal data corresponding to a plurality of nucleic acid sequences processed by a nucleic acid sequencing system;

processing, by the one or more computing devices, the training data using one or more neural networks to generate one or both of a confidence level and a basecalling prediction for each base in the plurality of nucleic acid sequences;

filtering, by the one or more computing devices, the training data to determine a filtered set of training data comprising fluorescence signal data corresponding to high-quality sequences in the plurality of nucleic acid sequences, wherein filtering comprises identifying the high-quality sequences using one or both of the confidence level and the basecalling prediction for each base in the plurality of sequences; and using, by the one or more computing devices, the filtered set of training data, to train one or more neural-network models to generate basecalling predictions;

wherein the one or more neural-network based models are included in one or more network blocks comprising a first network block and a second network block, and wherein generating one or both of a confidence level and a basecalling prediction comprises:

determining one or more first passing indices and a dataset quality index using one or more neural-network based models of the first network block, providing the first passing indices to one or more neural-network based models of the second network block, providing the dataset quality index to a sequence filter of the second network block; and determining, based on the one or more neural-network based models of the second network block, confidence level scores associated with bases included in sequences received by the second network block.

15. The non-transitory computer readable medium of claim 14 wherein identifying a high-quality sequence of the high-quality sequences comprises, with respect to a sequence of the plurality of nucleic acid sequences:

comparing the confidence level of each base in the sequence to a confidence level threshold to determine if each base is a high-quality base;

counting a number of high-quality bases in the sequence; and determining, based on the number of high-quality bases in the sequence, if the sequence is a high-quality sequence.

16. The non-transitory computer readable medium of claim 14 wherein the training data comprises labeled basecalling data, and wherein identifying a high-quality sequence of the high-quality sequences comprises, with respect to a sequence of the plurality of nucleic acid sequences:

determining, based on labeled basecalling data, if bases included in the sequence are correctly classified in the labeled basecalling data;

counting a number of correctly-classified bases in the sequence; and determining, based on the number of correctly-classified bases in the sequence, if the sequence is a high-quality sequence to determine if the sequence passes filtering.

17. The non-transitory computer readable medium of claim 16 wherein the one or more instructions cause the at least one computing device to perform processing comprising:

obtaining a retraining dataset including only sequences that passed filtering;

retraining the one or more neural network models using the retraining dataset to obtain one or more retained neural-network models;

re-determining confidence level scores and basecalling predictions based on the one or more retrained neural-network models; and filtering the retraining data based on one or more re-determined confidence level scores and basecalling predictions.

* * * * *